US008580918B2

(12) United States Patent
Alagarsamy et al.

(10) Patent No.: US 8,580,918 B2
(45) Date of Patent: Nov. 12, 2013

(54) PEPTIDIC GLP-2 AGONISTS

(75) Inventors: Sudarkodi Alagarsamy, San Diego, CA (US); Guangcheng Jiang, San Diego, CA (US); Pierre Riviere, San Diego, CA (US); Claudio Daniel Schteingart, San Diego, CA (US); Javier Sueiras-Diaz, La Jolla, CA (US); Kazimierz Wisniewski, San Diego, CA (US)

(73) Assignee: Ferring B.V., Hoofddorp (NL)

( * ) Notice: Subject to any disclaimer, the term of this patent is extended or adjusted under 35 U.S.C. 154(b) by 0 days.

(21) Appl. No.: 13/503,010

(22) PCT Filed: Oct. 21, 2010

(86) PCT No.: PCT/US2010/053570
§ 371 (c)(1),
(2), (4) Date: Apr. 19, 2012

(87) PCT Pub. No.: WO2011/050174
PCT Pub. Date: Apr. 28, 2011

(65) Prior Publication Data
US 2012/0231999 A1   Sep. 13, 2012

Related U.S. Application Data

(60) Provisional application No. 61/254,490, filed on Oct. 23, 2009.

(30) Foreign Application Priority Data

Oct. 23, 2009 (EP) ..................................... 09173900

(51) Int. Cl.
| A61K 38/00 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |

(52) U.S. Cl.
USPC ........................................................ 530/300

(58) Field of Classification Search
None
See application file for complete search history.

(56) References Cited

U.S. PATENT DOCUMENTS

| 5,990,077 | A | 11/1999 | Drucker | |
| 7,049,284 | B2 | 5/2006 | Drucker | |
| 2001/0027180 | A1 | 10/2001 | Isaacs | |
| 2003/0162703 | A1* | 8/2003 | Drucker et al. | 514/12 |
| 2007/0117752 | A1 | 5/2007 | Larsen et al. | |

FOREIGN PATENT DOCUMENTS

| WO | WO 96/32414 | 10/1996 |
| WO | WO 97/39031 | 10/1997 |
| WO | WO 9739031 A1 * | 10/1997 |
| WO | WO 98/03547 A1 | 1/1998 |
| WO | WO 02/066511 A2 | 8/2002 |
| WO | WO 2006/117565 A2 | 11/2006 |
| WO | WO 2008/056155 A1 | 5/2008 |

OTHER PUBLICATIONS

Amin, H., et al., "Functional Ontogeny of the Proglucagon-Derived Peptide Axis in the Premature Human Neonate," Pediatrics, 2008, pp. e180-e186, vol. 121.
Benjamin, M.A., et al., "Glucagon-like peptide-2 enhances intestinal epithelial barrier function of both transcellular and paracellular pathways in the mouse," GUT, 2000, pp. 112-119, vol. 47.
Boushey, R., et al., "Glucagon-like Peptide (GLP)-2 Reduces Chemotherapy-associated Mortality and Enhances Cell Survival in Cells Expressing a Transfected GLP-2 Receptor," Cancer Research, Jan. 15, 2001, pp. 687-693, vol. 61.
Cani, P.D., et al., "Changes in gut microbiota control inflammation in obese mice through a mechanism involving GLP-2- driven improvement of gut permeability," Gut, Oct. 9, 2009, pp. 1091-1103, vol. 58.
Dhanvantari, S., et al., "Role of Prohormone Convertases in the Tissue-Specific Processing of Proglucagon," Molecular Endocrinology, 1996, pp. 342-355, vol. 10, No. 4.
Drozdowski, L., et al., "Aging and the intestine," World Journal of Gastroenterology, Dec. 21, 2006, pp. 7578-7584, vol. 12, No. 47.
Estall, J., et al., "Glucagon-Like Peptide-2," Annu. Rev. Nutr., Feb. 24, 2006, pp. 391-411, vol. 26.
Jeppsesen, P.B., et al., "Short Bowel Patients Treated for Two Years with Glucagon-Like Peptide 2: Effects on Intestinal Morphology and Absorption, Renal Function, Bone and Body Composition, and Muscle Function," Gastroenterology Research and Practice, Mar. 24, 2009, pp. 1-12.
Lovshin, J.A., et al., "Extrahypothalamic Expression of the Glucagon-Like Peptide-2 Receptor Is Coupled to Reduction of Glutamate-Induced Cell Death in Cultured Hippocampal Cells," Endocrinology, Jul. 2004, pp. 3495-3506, vol. 145, No. 7.
Mojsov, S., et al., "Preproglucagon Gene Expression in Pancreas and Intestine Diversifies at the Level of Post-translational Processing," Journal of Biological Chemistry, Sep. 5, 1986, pp. 11880-11889, vol. 261, No. 25.
Newberry, E., et al., "Intestinal Lipid Absorption, GLP-2, and CD36: Still More Mysteries to Moving Fat," Gastroenterology, 2009, pp. 775-778.
Wideman, R., et al., "A Switch from PC2 to PC1/3 Expression in Transplanted α-cells is Accompanied by Differential Processing of Proglucagon and Improved Glucose Homeostasis in Mice Running Title: Transplantation of PC2-or PC1/3-expressing α-cells," pp. 1-24.
PCT International Search Report and Written Opinion, PCT/US2010/053570, Feb. 14, 2011, 9 Pages.
Dacambra, M., et al., "Structural Determinants for Activity of Glucagon-like Peptide-2," Biochemistry, 2000, pp. 8888-8894, vol. 39.
Supplementary European Search Report for European Patent Application No. EP 10825678, Apr. 15, 2013, 7 Pages.

* cited by examiner

Primary Examiner — Marcela M Cordero Garcia
Assistant Examiner — Kaipeen Yang
(74) Attorney, Agent, or Firm — Fenwick & West LLP

(57) ABSTRACT

Novel GLP-2 analogs with improved pharmacokinetic properties are described as well as their use in the treatment of disease.

36 Claims, No Drawings

PEPTIDIC GLP-2 AGONISTS

FIELD OF THE INVENTION

The present invention relates to novel compounds with agonist activity at the GLP-2 receptor, pharmaceutical compositions comprising these, and use of the compounds for the manufacture of medicaments for treatment of diseases.

BACKGROUND

Glucagon-like peptide 2 (GLP-2) is a 33 amino-acid gastrointestinal (GI) hormone that is produced by enteroendocrine cells in the small and large intestine and released into circulation after meals. GLP-2 is also expressed in cerebral cortex and astrocytes. GLP-2 exerts its biological responses through specific GLP-2 receptors. GLP-2 is derived from proglucagon processed by prohormone convertase (PC) 1/3. This processing also results in GLP-1, glycentin and oxyntomodulin. When processed in the alpha cells of the pancreas by PC 2, processing of proglucagon results in glucagon.

Overall, GLP-2 coordinates a broad variety of important GI responses including mucosal trophic effect and an increase in intestinal absorption and nutrient assimilation (Lovshin, J. and D. J. Drucker, *Ped. Diabetes,* 1(1):49-57, 2001); anti-inflammatory activities; mucosal healing and repair; decreasing intestinal permeability to bacteria; and an increase in mesenteric blood flow (Bremholm, L. et al. *Scan. J. Gastro.* 44(3):314-319, 2009). Such properties are expected to provide therapeutic benefits in a variety of conditions.

GLP-2 plays a role in the intestine from before birth. Various studies of human and animal neonates and infants have examined the role of GLP-2 in intestinal development. GLP-2 is found to be present in human cord blood at birth at levels comparable to adult fasting levels. (Bode, S., et al. *Neonatology* 91(1) 49-53, 2007.) GLP-2 is secreted in response to feeding and the mechanism by which GLP-2 is secreted is considered to be established at 24 weeks for human neonates. (Yoshikawa, H., et al. *Pediatrics Intl.* 48(5):464-469, 2006.) GLP-2 and the other proglucagon-derived peptides have role in normal intestinal development and nutrient handling. (Amin, H., et al. *Pediatrics* 121(1):e180-e186, 2008.) It has also been determined that GLP-2 levels are decreased in preterm infants with feeding intolerance. Therefore, GLP-2 may have therapeutic benefits for such preterm infants. (Ozer, E. A., et al. *J. Trop. Pediatr.* 55(4): 276-277, 2009.) Necrotizing enterocolitis (NEC) is another condition associated with preterm infants and GLP-2 is associated with protecting against NEC in rats and pigs. (Izumi, H., et al. *J. Nutr.* 139 (7):1322-1327, 2009 and Sangild, P. T., et al. *Gastroenterology.* 130(6):1776-1792, 2006.) Parenterally fed neonatal pigs suffer from arginine deficiency. Piglets who received additional GLP-2 infusions showed improved levels of arginine synthesis as well as improvements in mucosal mass and villus height in the small intestine. (Urschel, K. L., et al. *J. Nutr.* 137:601-606, 2007.)

GLP-2 may be of therapeutic benefit to patients with various intestinal conditions including intestinal damage and insufficiency. Specifically, it is suggested that diseases involving malabsorption, inflammation and/or mucosal damage could be ameliorated by treatment with GLP-2. Review articles that give an overview of the therapeutic benefits of GLP-2 include Ziegler, T. R., et al. *J Parenter. Enteral Nutr.* 23(6 Suppl):S174-S183, 1999; Drucker, D. J., et al. *J Parenter. Enteral Nutr.* 23(5 Suppl):598-100, 1999; and Estall and Drucker, *Ann. Rev. Nutr.* 26:391-411, 2006.

Inflammation is a symptom of colitis and the functional changes in the intestine that persist even after resolution of the inflammation have been found to include an increase in GLP-2 immunoreactive L cells. (Lomax, A. E., et al. *Am. J. Physiol. Gastrointest. Liver Physiol.* 292:G482-G491, 2007.) Treatment of mice with colitis with GLP-2 resulted in a reversal of weight loss, reduction of interleukin-1 expression, and increase of colon length, crypt depth, and mucosal area. This demonstrates that GLP-2 can aid healing of the intestine even in the presence of active inflammation of the intestine. (Drucker, D. J., et al. *Am. J. Physiol. Gastrointest. Liver Physiol.* 276(1):G79-G91, 1999.) Celiac disease also involves inflammation of the intestine. Studies of humans with celiac disease indicate that GLP-2 may be part of the mucosal healing mechanism for patients with celiac disease. (Caddy, G. R., et al. *Eur. J. Gastroenterol. Hepatol.* 18(2): 195-202, 2006.) Mice with colitis showed reduced inflammation after treatment with GLP-2. Additionally, the mechanism of the anti-inflammatory activity is GLP-2 activation of the suppressor of cytokine signaling (SOCS) 3 pathway. (Ivory, C. P. A., et al. *Am. J. Physiol. Gastrointest. Liver Physiol.* 295:G1202-G1210, 2008.) As SOCS3 may be involved in tumor suppression (Lund, P. K. and R. J. Rigby, *Gastroenterology* 131(1):317-319, 2006), GLP-2 activation of the SOCS3 pathway shows that GLP-2 may have protective effects against intestinal cancers.

Barrier function of the epithelial layer of the small intestine is relevant to a number of disorders. Examples include sepsis and bacterial peritonitis. GLP-2 reduces the permeability of the epithelial lining of the small intestine as well as decreasing apoptosis in crypts and villi in the small intestine. (Lovshin and Drucker.) GLP-2's protective effect on the barrier function of the epithelial lining has been shown in burn patients in China. (Wang, S. L. *Zhonghua Shoo Shang Za Zhi* 24(5):396-9, 2008.) In acute pancreatitis, there is a generalized inflammatory response and the permeability of the intestine increases leading to an increase in transport of bacteria through the epithelium of the intestine. Treatment with GLP-2 in rats with acute pancreatitis decreased intestinal permeability. (Kouris, G. J., et al. *Am. J. Surgery* 181(6):571-575, 2001.) Additionally, administration of GLP-2 in mice with acute pancreatitis improved immunological function of the intestine. (Kong, L. S., et al. *Zhongguo Wei Zhong Bing Ji Jiu Yi Xue.* 21(2):103-106, 2009.) Stress-induced reduction in intestinal barrier function in mice has also improved by treatment with GLP-2. (Cameron, H. L. and M. H. Perdue. *J Pharmacol Exp Ther.* 314(1):214-220, 2005.) Specifically, it has been determined that the treatment with GLP-2 improves barrier function by affecting both the paracellular and transcellular pathways. (Benjamin, M. A., et al. *Gut* 47:112-119, 2000.) Reduced barrier function has also been implicated in immediate hypersensitivity and late-phase allergic inflammation. (Cameron, H. L., et al. *Am. J. Physiol. Gastrointest. Liver Physiol.* 284(6):G905-G912, 2003.) Gut barrier function is compromised in diabetic and obese mice leading to metabolic disorders in such mice. Increasing endogenous GLP-2 production in such mice leads to improvement of gut barrier function. (Cani, P. D., et al. *Gut* 58:1091-1103, 2009.)

Malabsorption in the elderly, which is believed to contribute to malnutrition in that population, has been shown to be reversed by GLP-2. (Drozdowski, L. and A. B. R. Thomson, *World J. Gastroenterol.* 12(47):7578-7584, 2006.) GLP-2 also regulates absorption of lipids in the intestine as well as the assembly and secretion of triglyceride-right lipoproteins from intestinal enterocytes. (Hsieh, J., et al. *Gastroentorology* 137(3):997-1005, 2009). Intestinal absorption of lipids was enhanced in humans during GLP-2 administration as evidenced by increased postprandial plasma concentrations of triglycerides and free fatty acids. (Meier, J. J., et al. *Gastroenterology* 130(1):44-54, 2006.) These results suggest GLP-2 as a treatment for steatorrhea.

Because GLP-2 is secreted in the intestine responsive to intake of food, when a patient's energy intake is other than enterally, the lack of GLP-2 can lead to various side effects in the intestines. Dysfunction in the intestines frequently accompanies cancer and its treatment. In children undergoing cancer treatment it was shown that if energy intake was enterally, the GLP-2 secretion remained normal. (Andreassen, B. U., et al. *J. Ped. Gastroenterol. Nutr.* 40(1):48-53, 2005.) In pre-term infants whose intestines are not fully developed, feeding is often mostly parenteral with some enteral to promote development of the intestines. Secretion of GLP-2 is important for that development and it has been determined that 40% of total nutrient intake should be enteral in order to ensure normal mucosal proliferation and growth. (Burrin, D. G., et al. *Am. J. Clin. Nutr.* 71(6):1603-10, 2000.)

Studies of rats on total parenteral nutrition (TPN) shows that TPN results in hypoplasia of the gut mucosa which in turn is associated with a reduction in immune response and an increase in translocation of bacteria from the gut to mesenteric lymph nodes, liver and spleen. Administration of GLP-2 protects against this side effect. (Chance, W. T. et al. *Am. J. Gastrointest. Liver Physiol.* 273:G559-G563, 1997; Chance, W. T., et al. *Peptides,* 27(4):883-892, 2006; and Kaji, T., et al. *Eur. J. Pharmacol.* 596(1-3):138-145.)

GLP-2 has been shown to be involved in the regulation of glucose and may have utility in the treatment of both diabetes and hypoglycemia. De Heer, et al. demonstrated that GLP-2 stimulates glucagon secretion in rat islets. (*Diabetologia* 50(10):2135-2142, 2007.) Glucagon in turn raises blood glucose levels. Wideman, et al. have shown that by altering the expression of PC in mouse alpha cells from PC2 to PC1/3, proglucagon is processed to yield the products of PC 1/3, (GLP-1, GLP-2, oxyntomodulin) rather than glucagon. The authors suggest therefore utility of GLP-2 in the treatment of diabetes. (*Diabetes* 56(11):2744-2752, 2007 and *Mol. Ther.* 17(1):191-198, 2008.)

GLP-2 has utility in the treatment of short bowel syndrome (SBS) and related conditions including intestinal failure. SBS patients treated with GLP-2 for two years showed improvement in various measures including improved renal function, reduction in fecal weight and maintenance of intestinal fluid and electrolyte absorption at lower oral intakes. Jeppesen, P. B., et al. *Gastroenterology Research and Practice,* 2009, Article 616054. In rats undergoing serial transverse enteroplasty (STEP) for treatment of SBS, postprandial levels of GLP-2 were increased as compared to rats with SBS rats who had not undergone STEP. Additionally, expression of GLP-2 receptor increased. The research suggests that GLP-2 would be useful in guiding use of the STEP procedure. (Kaji, T., et al. *J. Ped. Surgery.* 44(8):1552-1559, 2009.) Intestinal adaptation after a resection is aided by GLP-2 in rats as well. (Perez, A., et al. *J Parenter. Enteral Nutr.* 29(2):97-101, 2005; Li, H., et al. *Zhonghua Wei Chang Wai Ke Za Zhi* 9(1):67-70, 2006; Kaji, T., et al. *J. Surg. Res.* 152(2):271-280, 2009; and Garrison, A. P., et al. *Am. J. Physiol. Gastrointest. Liver Physiol.* 296:G643-G650, 2009.)

Intestines can be damaged through both chemotherapy and radiation treatment for cancer. Administration of teduglutide (a GLP-2 analog) prior to gamma irradiation showed a protective effect in mice. (Booth, C., et al. *Cell Proliferation* 37(6):385-400, 2004.) See also Tones, S., et al. *Int J Radiat Oncol Biol Phys.* 69(5):1563-1571, 2007. GLP-2 treatment also has a protective effect on the intestine during chemotherapy and aids recovery from damage related to chemotherapy. (Boushey, R. P., et al. *Cancer Res.* 61:687-693, 2001 and Tavakkolizadeh, A., et al. *J. Surg. Res.* 91(1):77-82, 2000.)

GLP-2 also mitigates damage to mouse intestines due to nonsteroidal anti-inflammatory drugs (NSAID). (Boushey, R. P., et al. *Am. J. Physiol. Endocrinol. Metab.* 277(5):E937-E947, 1999.)

GLP-2 is also implicated in gastric relaxation of mice. (Amato, A., et al. *Am. J. Physiol. Gastrointest. Liver Physiol.* 296:G678-G684, 2009.) Additionally GLP-2 inhibits antral emptying in humans. (Nagell, C. F., et al. *Scan. J. Gastroenterol.* 39(4):353-358, 2004.) Also related to appetite, GLP-2 inhibits ghrelin secretion in humans. (Banasch, M., et al. *Reg. Peptides.* 137(3):173-178, 2006.)

GLP-2 has been studied in the brain as well. GLP-2 is involved in astroglial regeneration in rats. (Velázquez, E., et al. *Eur. J. Biochem.* 270(4):3001-3009, 2003 and Velázquez, E., et al. *Mol. Neurobiol.* 40:183-193, 2009.) GLP-2 has been shown to have a cytoprotective effect on cells derived from rat central nervous system. (Lovshin, J. A., et al. *Endocrinology.* 145(7):3495-3506, 2004.) GLP-2 has been shown to have anti-depressant effects in mice. (Iwai, T., et al. *Behavioural Brain Res.* 204(1):235-240, 2009.) Vrang, N., et al. investigated subgroups of GLP-containing neurons and their functions.) *Brain Res.* 1149:118-126, 2007.)

GLP-2 has further been shown to be effective in treating osteoporosis. (Henriksen, et al. *Bone,* 45(5):833-42, 2009.)

Additional research on GLP-2 has investigated GLP-2 and autism (Robertson, M. A., et al. *J. Autism Dev. Disord.* 38:1066-1071, 2008), GLP-2 and cAMP levels in 3T3-L1 adipocytes (Montrose-Rafizadeh, C. et al. *J. Cell. Physiol.* 172(3):275-283, 1998)

Native GLP-2 is however not a suitable drug candidate as it is rapidly degraded by peptidases (e.g. DPP IV). It therefore has a very short half-life ($t_{1/2}$=10 min. in humans) and rapid clearance (CL). Certain GLP-2 analogs with somewhat improved CL relative to hGLP-2 have been created and progressed to clinical development, including [Gly2]hGLP 2 (teduglutide) and ZP-1846 and ZP-1848. (PCT Publication No. WO/2006/117565) Though improved over native GLP-2, it is believed that their pharmacokinetic properties still do not allow for optimal drug dosing, limiting their clinical utility. Therefore, GLP-2 analogs with improved pharmacokinetic properties are needed.

SUMMARY OF THE INVENTION

Provided are compounds, compositions comprising the compounds, and methods of using compounds, wherein the compounds are agonists of the GLP-2 receptor and have improved pharmacokinetic properties as compared to currently available GLP-2 analogs.

According to one embodiment, compounds of the present invention have the general formula I:

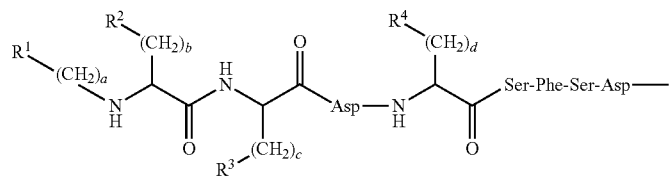

-continued

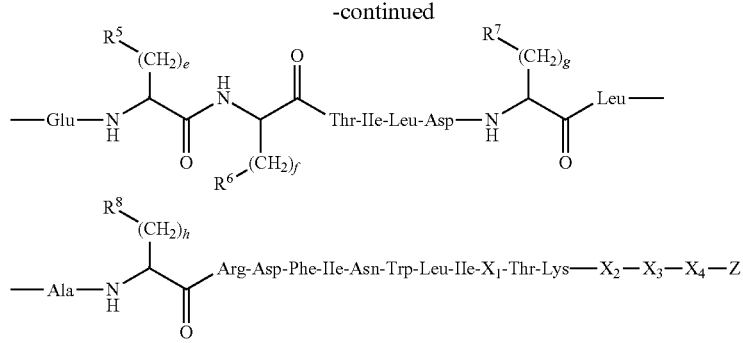

wherein:
R¹ is chosen from the group consisting of H, alkyl, aralkyl and aryl;
a is chosen from the group consisting of 0, 1, 2, 3, 4, 5, 6, and 7;
R² is a heteroaryl;
b is 1 or 2;
R³ and R⁴ are each independently selected from the group consisting of H and alkyl;
c and d are each independently chosen from the group consisting of 0 and 1;
R⁵ is chosen from the group consisting of H and alkyl;
e is chosen from the group consisting of 1, 2, 3, and 4;
R⁶ is chosen from the group consisting of H, alkyl, cycloalkyl, aryl, biaryl, heteroaryl, and —C(O)—NH₂;
f is chosen from the group consisting of 0, 1, 2, and 3, with the proviso that if R⁶ is other than H, f is not 0;
R⁷ is chosen from the group consisting of alkyl, cycloalkyl, aryl, biaryl, diaryl, heteroaryl and —C(O)—NH₂;
g is chosen from the group consisting of 1, 2, and 3;
R⁸ is chosen from the group consisting of H, alkyl, —CH(OH)—CH₃;
h is chosen from the group consisting of 0, 1, 2, and 3;
X₁ is Gln or Arg;
X₂, X₃, and X₄ are each independently present or absent and if present, independently selected from the group consisting of Val, Leu, Ile, Ser, Thr, Asp, and Glu; and
Z is NR⁹R¹⁰ or OH, wherein:
  R⁹ and R¹⁰ are each independently selected from the group consisting of hydrogen, alkyl, heteroalkyl, cycloalkyl, aryl, heteroaryl, heteroaralkyl, aralkyl, and —(CH₂)ₓ—[(CH₂)₂—O]ᵧ—(CH₂)ₓ—[NH—C(O)—CH₂—O—CH₂]_z—C(O)—NHR¹¹, wherein:
    R¹¹ is H or —[(CH₂)₂—O]ᵧ—(CH₂)ₓ—C(O)—NH₂
    each x is independently selected from the group consisting of 0, 1, 2, and 3,
    each y is independently selected from the group consisting of 3, 4, 5, and 6,
    z is 0 or 1, and
    R⁹ and R¹⁰ are optionally joined to form a 4- to 7-membered ring which may be a heterocycle or a heteroaryl;
and pharmaceutically acceptable salts thereof.

In one embodiment the compound is of formula I wherein R⁶ and f can not result in L-Asn.
In one embodiment the compound is of formula I wherein R⁷ and g can not result in L-Asn.
In one embodiment the compound is of formula I wherein R⁵ and e form Nle.
In one embodiment the compound is of formula I wherein the combination of R⁶ and f and the combination of R⁷ and g can not both result in amino acids chosen from the group consisting of Gly, L-Ala, L-Asn, L-Gln, L-Ser, L-Phe, L-Leu, L-Ile, L-Val and L-His.

In one embodiment the compound is of formula I wherein R¹ is H, a is 0, R² is

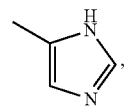

and b is 1. This yields histidine at the N terminus of the compound.
In one embodiment the compound is of formula I wherein X₂, X₃, and X₄ are all absent.
In one embodiment the compound is of formula I wherein X₂, X₃, and X₄ are all present.
In one embodiment the amino acid formed with the side chain at R⁶ is in the D configuration.
In one embodiment the amino acid formed with the side chain at R⁷ is in the D configuration.
In one embodiment, the compound is example compound 8 of Table 1 wherein amino acid in position 16 is in the D configuration as shown in Table 1. Alternatively, the compound is compound 12, 13, 29, 30, 32, 35, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 of Table 1 wherein for each example, the amino acid at position 11 is in the D configuration as shown in Table 1.
In one embodiment the compound is of formula I wherein Z is NH₂ or OH.
In one embodiment the compound is of formula I wherein Z is NR⁹R¹⁰ and one of R⁹ and R¹⁰ is hydrogen.
In one embodiment the compound is of formula I wherein c is 0 and R³ is H.
In one embodiment the compound is of formula I wherein e is 3, R⁵ is methyl, f is 1, R⁶ is phenyl, g is 1, R⁷ is isopropyl, X₂ is Ile, X₃ is Thr, X₄ is Asp and Z is NH₂ or OH.
In one embodiment the compound is of formula I wherein R³ is hydrogen, c is 0, R⁵ is methyl, e is 3, R⁶ is phenyl or 2-thienyl, f is 1, R⁷ is phenyl or isopropyl, g is 1, R⁸ is H or —CH(OH)—CH₃ and h is 0 or 1.
In one embodiment the compound is of formula I wherein Z is NR⁹R¹⁰ and R⁹ is hydrogen and R¹⁰ is aralkyl or alkyl.
In one embodiment the compound is selected from the group consisting of:

```
His-Gly-Asp-Gly-Ser-Phe-Ser-Asp-Glu-Nle-D-Thi-Thr-
Ile-Leu-Asp-Phe-Leu-Ala-Ala-Arg-Asp-Phe-Ile-Asn-
```

-continued

Trp-Leu-Ile-Gln-Thr-Lys-NH₂,

His-Gly-Asp-Gly-Ser-Phe-Ser-Asp-Glu-Nle-D-Phe-Thr-
Ile-Leu-Asp-Phe-Leu-Ala-Ala-Arg-Asp-Phe-Ile-Asn-
Trp-Leu-Ile-Gln-Thr-Lys-NH₂,

His-Gly-Asp-Gly-Ser-Phe-Ser-Asp-Glu-Nle-D-Phe-Thr-
Ile-Leu-Asp-Leu-Leu-Ala-Ala-Arg-Asp-Phe-Ile-Asn-
Trp-Leu-Ile-Gln-Thr-Lys-Ile-Thr-Asp-NH₂,

His-Gly-Asp-Gly-Ser-Phe-Ser-Asp-Glu-Nle-D-Phe-Thr-
Ile-Leu-Asp-Leu-Leu-Ala-Ala-Arg-Asp-Phe-Ile-Asn-
Trp-Leu-Ile-Gln-Thr-Lys-Ile-Thr-Asp-NHEt,

His-Gly-Asp-Gly-Ser-Phe-Ser-Asp-Glu-Nle-D-Phe-Thr-
Ile-Leu-Asp-Leu-Leu-Ala-Ala-Arg-Asp-Phe-Ile-Asn-
Trp-Leu-Ile-Gln-Thr-Lys-Ile-Thr-Asp-NH-4-Pic,

His-Gly-Asp-Gly-Ser-Phe-Ser-Asp-Glu-Nle-D-Phe-Thr-
Ile-Leu-Asp-Leu-Leu-Ala-Ala-Arg-Asp-Phe-Ile-Asn-
Trp-Leu-Ile-Gln-Thr-Lys-Ile-Thr-Asp-NH-((CH₂)₂O)₄—
(CH₂)₂—CO-NH₂,

His-Gly-Asp-Gly-Ser-Phe-Ser-Asp-Glu-Nle-D-Phe-Thr-
Ile-Leu-Asp-Leu-Leu-Ala-Ala-Arg-Asp-Phe-Ile-Asn-
Trp-Leu-Ile-Gln-Thr-Lys-Ile-Thr-Asp-NH-CH₂—
((CH₂)₂O)₃—(CH₂)₃—NHCO—CH₂—O—CH₂—CO-NH₂,
and His-Gly-Asp-Gly-Ser-Phe-Ser-Asp-Glu-Nle-D-Phe-Thr-
Ile-Leu-Asp-Leu-Leu-Ala-Ala-Arg-Asp-Phe-Ile-Asn-
Trp-Leu-Ile-Gln-Thr-Lys-Ile-Thr-Asp-NH-isobutyl.

In one embodiment the compound is selected from the group consisting of:

His-Gly-Asp-Gly-Ser-Phe-Ser-Asp-Glu-Nle-D-Phe-Thr-
Ile-Leu-Asp-Leu-Leu-Ala-Ala-Arg-Asp-Phe-Ile-Asn-
Trp-Leu-Ile-Gln-Thr-Lys-Ile-Thr-Asp-OH,

His-Gly-Asp-Gly-Ser-Phe-Ser-Asp-Glu-Nle-D-Phe-Thr-
Ile-Leu-Asp-Phe-Leu-Ala-Ala-Arg-Asp-Phe-Ile-Asn-
Trp-Leu-Ile-Gln-Thr-Lys-Ile-Thr-Asp-NH-CH₂—
((CH₂)₂O)₃—(CH₂)₃—NHCO—CH₂—O—CH₂-CONH₂,

His-Gly-Asp-Gly-Ser-Phe-Ser-Asp-Glu-Nle-D-Phe-Thr-
Ile-Leu-Asp-Phe-Leu-Ala-Ala-Arg-Asp-Phe-Ile-Asn-
Trp-Leu-Ile-Gln-Thr-Lys-Ile-Thr-Asp-NH-CH₂—
((CH₂)₂O)₃—(CH₂)₃—NHCO—CH₂—O—CH₂—CONH—((CH₂)₂O)₆—
(CH₂)₂-CONH₂,

His-Gly-Asp-Gly-Ser-Phe-Ser-Asp-Glu-Nle-D-Thi-Thr-
Ile-Leu-Asp-Leu-Leu-Ala-Thr-Arg-Asp-Phe-Ile-Asn-
Trp-Leu-Ile-Gln-Thr-Lys-Ile-Thr-Asp-NH₂,

His-Gly-Asp-Gly-Ser-Phe-Ser-Asp-Glu-Nle-D-Phe-Thr-
Ile-Leu-Asp-Phe-Leu-Ala-Ala-Arg-Asp-Phe-Ile-Asn-
Trp-Leu-Ile-Gln-Thr-Lys-Ile-Thr-Asp-NH₂,

His-Gly-Asp-Gly-Ser-Phe-Ser-Asp-Glu-Nle-D-Phe-Thr-
Ile-Leu-Asp-Phe-Leu-Ala-Ala-Arg-Asp-Phe-Ile-Asn-
Trp-Leu-Ile-Gln-Thr-Lys-Ile-Thr-Asp-OH,
and His-Gly-Asp-Gly-Ser-Phe-Ser-Asp-Glu-Nle-D-Thi-Thr-
Ile-Leu-Asp-Phe-Leu-Ala-Ala-Arg-Asp-Phe-Ile-Asn-
Trp-Leu-Ile-Gln-Thr-Lys-Ile-Thr-Asp-NH₂.

Also provided is a pharmaceutical composition comprising one or more compounds of the invention optionally in association with a pharmaceutically acceptable adjuvant, diluent or carrier.

Also provided are methods of treating one of the group consisting of gastrointestinal injury, diarrheal diseases, intestinal insufficiency, acid-induced intestinal injury, arginine deficiency, idiopathic hypospermia, obesity, celiac disease, catabolic illness, chemotherapy-induced enteritis, febrile neutropenia, diabetes, obesity, fat malabsorption, steatorrhea, autoimmune diseases, food allergies, gastric ulcers, hypoglycemia, gastrointestinal barrier disorders, sepsis, bacterial peritonitis, burn-induced intestinal damage, decreased gastrointestinal motility, inflammatory bowel disease, intestinal failure, chemotherapy-associated bacteremia, bowel trauma, bowel ischemia, mesenteric ischemia, irritable bowel syndrome, short bowel syndrome, malnutrition, necrotizing enterocolitis, necrotizing pancreatitis, neonatal feeding intolerance, NSAID-induced gastrointestinal damage, nutritional insufficiency, total parenteral nutrition damage to gastrointestinal tract, neonatal nutritional insufficiency, radiation-induced enteritis, radiation-induced injury to the intestines, mucositis, pouchitis, ischemia, and stroke, the method comprising administering to an animal patient in need thereof, a therapeutically effective amount of a compound of the invention, wherein an animal includes a human. Inflammatory bowel disease includes, but is not limited to, Crohn's Disease and ulcerative colitis.

Also provided are methods of regulating appetite; enhancing, stimulating or accelerating weight loss; enhancing, stimulating or accelerating gastric relaxation; controlling glucose levels; enhancing, stimulating or accelerating hunger satiety; enhancing intestinal immune function; enhancing, stimulating or accelerating intestinal wound healing; enhancing, stimulating or accelerating juvenile weight loss; enhancing, stimulating or accelerating weight loss; enhancing, stimulating or accelerating neonatal bowel development; enhancing, stimulating or accelerating fetal or neonatal development; preventing intestinal cancers; enhancing or stimulating mucosal integrity; minimizing, mitigating, or preventing bacterial translocation in the intestines; enhancing, stimulating or accelerating recovery of the intestines after surgery; preventing relapses of inflammatory bowel disease, including Crohn's Disease and ulcerative colitis, e.g. after surgery; or achieving or maintaining energy homeostasis, the method comprising administering to an animal patient in need thereof, a therapeutically effective amount of a compound of the invention wherein an animal includes a human.

Also provided are methods of treating one of the group consisting of depression, autism, osteoporosis, and traumatic brain injury, the method comprising administering to an animal patient in need thereof, a therapeutically effective amount of a compound of the invention wherein an animal includes a human.

Also provided are methods of enhancing, stimulating or accelerating astroglial regeneration or enhancing, stimulating or accelerating repair or growth of the central nervous system; the method comprising administering to an animal patient in need thereof, a therapeutically effective amount of a compound of the invention wherein an animal includes a human.

Also provided are uses of a compound of the invention for the manufacture of a medicament for treating one of the group consisting of gastrointestinal injury, diarrheal diseases, intestinal insufficiency, acid-induced intestinal injury, arginine deficiency, idiopathic hypospermia, obesity, celiac disease, catabolic illness, chemotherapy-induced enteritis, febrile neutropenia, diabetes, obesity, fat malabsorption, steatorrhea, autoimmune diseases, food allergies, gastric ulcers, hypoglycemia, gastrointestinal barrier disorders, sepsis, bacterial peritonitis, burn-induced intestinal damage, decreased gastrointestinal motility, inflammatory bowel disease, intestinal failure, chemotherapy-associated bacteremia, bowel trauma, bowel ischemia, mesenteric ischemia, irritable bowel syndrome, short bowel syndrome, malnutrition, necrotizing enterocolitis, necrotizing pancreatitis, neonatal feeding intolerance, NSAID-induced gastrointestinal damage, nutritional insufficiency, total parenteral nutrition damage to gastrointestinal tract, neonatal nutritional insufficiency, radiation-induced enteritis, radiation-induced injury to the intestines, mucositis, pouchitis, ischemia, and stroke. Inflammatory bowel disease includes, but is not limited to, Crohn's Disease and ulcerative colitis.

Also provided are uses of a compound of the invention for the manufacture of a medicament for regulating appetite; enhancing, stimulating or accelerating weight loss; enhancing, stimulating or accelerating gastric relaxation; controlling glucose levels; enhancing, stimulating or accelerating hunger satiety; enhancing intestinal immune function; enhancing, stimulating or accelerating intestinal wound healing; enhancing, stimulating or accelerating juvenile weight loss; enhancing, stimulating or accelerating weight loss; enhancing, stimulating or accelerating neonatal bowel development; enhancing, stimulating or accelerating fetal or neonatal development; preventing intestinal cancers; enhancing or stimulating mucosal integrity; minimizing, mitigating, or preventing bacterial translocation in the intestines; enhancing, stimulating or accelerating recovery of the intestines after surgery; preventing relapses of inflammatory bowel disease, including Crohn's Disease and ulcerative colitis, e.g. after surgery; or achieving or maintaining energy homeostasis.

Also provided are uses of a compound of the invention for the manufacture of a medicament for treating one of the group consisting of depression, autism, osteoporosis, and traumatic brain injury.

Also provided are uses of a compound of the invention for the manufacture of a medicament for enhancing, stimulating or accelerating astroglial regeneration or enhancing, stimulating or accelerating repair or growth of the central nervous system.

DETAILED DESCRIPTION

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (2007) *Advanced Organic Chemistry* 5$^{th}$ *Ed.* Vols. A and B, Plenum Press, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology, within the skill of the art.

"Alkyl" is an optionally substituted $C_{1-6}$ straight chain alkyl or optionally substituted $C_{3-8}$ branched chain alkyl, including iso-, sec-, and tert-configurations.

"Aryl" is an optionally substituted mono- or bi-cyclic aromatic carbocyclic ring system of 5-12 carbon atoms. Exemplary mono- and bi-cyclic aromatic carbocyclic ring systems include optionally substituted phenyl and optionally substituted naphthyl.

"Biaryl" is —Ar—Ar wherein Ar is an aryl group.

"Diaryl" is

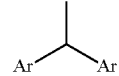

wherein Ar is an aryl group.

"Aralkyl" is an alkyl group which has as a substituent an aryl group.

"Heteroaryl" is an optionally substituted aromatic heterocyclic five- or six-membered ring system. A five-membered heteroaromatic ring system is a monocyclic aromatic ring system having five ring atoms, wherein 1, 2, 3 or 4 ring atoms are independently selected from N, O and S. Exemplary five-membered heteroaromatic ring systems include optionally substituted imidazolyl, thiazolyl, thienyl, furyl, pyrazolyl, and triazolyl. A six-membered heteroaromatic ring system is a monocyclic aromatic ring system having six ring atoms, wherein 1, 2, 3 or 4 ring atoms are independently selected from N, O and S. Exemplary six-membered heteroaromatic ring systems include optionally substituted pyridyl, pyrimidyl and pyrazinyl.

Optionally substituted means that there may be one or more substituent group present on a specified moiety. The substituent moieties may be for example fluorine (F), chlorine (Cl) and bromine (Br) atoms and alkyl, hydroxy (—OH), alkoxy (—O-alkyl), alkylthio (—S-alkyl), cyano (—CN), amino (—NH$_2$), amido (—C(O)—NH$_2$), carboxyl (—C(O)—OH) and $C_{1-6}$ alkyl ester (—C(O)—O-alkyl).

Examples of pharmaceutically acceptable salts include acid addition salts, e.g. a salt formed by reaction with hydrohalogen acids such as hydrochloric acid and mineral acids, such as sulphuric acid, phosphoric acid and nitric acid, as well as aliphatic, alicyclic, aromatic or heterocyclic sulphonic or carboxylic acids such as formic acid, acetic acid, propionic acid, succinic acid, glycolic acid, lactic acid, malic acid, tartaric acid, citric acid, benzoic acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halobenzenesulphonic acid, trifluoroacetic acid, trifluoromethanesulphonic acid, toluenesulphonic acid and naphthalenesulphonic acid. (see, e.g., Berge et al., *J. Pharm. Sci.* 66:1-19, 1977 and Wermuth, C. G. and P. H. Stahl, eds. *Pharmaceutical Salts: Properties, Selection and Use.* Zurich: Verlag Helvetica Chimica Acta, 2002)

Abbreviations used are:

| Abbreviation | Conventional Name |
| --- | --- |
| Bu | butyl-alkyl residues may be further denoted as n (normal, i.e. unbranched), i (iso), s (sec) and t (tertiary) |
| Bzl | Benzyl |
| $CH_3CN$ | Acetonitrile |
| DCM | Dichloromethane |
| DIAD | N,N'-Diisopropyl azodicarboxylate |
| DIC | N,N'-Diisopropylcarbodiimide |
| DIPEA | N,N-diisopropylethylamine |
| DMF | N,N-dimethylformamide |
| Et | Ethyl |
| Fmoc | 9-fluorenylmethoxycarbonyl |
| GLP | glucagon-like peptide |
| GLP-1 | glucagon-like peptide 1 |
| GLP-2 | glucagon-like peptide 2 |
| GLP-2 receptor | glucagon-like peptide 2 receptor |
| h | hour(s) |
| HATU | N-[(dimethylamino)-1H-1,2,3-triazolo[4,5-b]pyridine-1-ylmethylene]-N-methylmethanaminium hexafluorophosphate N-oxide |
| hGLP | human glucagon-like peptide |
| hGLP-1 | human glucagon-like peptide 1 |
| hGLP-2 | human glucagon-like peptide 2 His-Ala-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:1) |
| hGLP-2 receptor | human glucagon-like peptide 2 receptor |
| HIPF | 1,1,1,3,3,3-hexafluoro-2-propanol |
| Hmb | 2-hydroxy-4-methoxybenzyl |
| HOAt | 1-hydroxy-7-azabenzotriazole |
| HOBt | N-hydroxybenzotriazole |
| HPLC | high performance liquid chromatography |
| i-Am | Isoamyl (3-methylbutyl) |
| LC | liquid chromatography |
| MS | mass spectrometry |
| µg | Microgram |
| NMP | N-methylpyrrolidone |
| Pal | peptide amide linker [5-(4-Fmoc-aminomethyl-3,5-dimethoxy-phenoxy)valeric acid] |
| PEG | polyethylene glycol |
| 4-Pic | 4-methylpyridyl (γ-picolyl or 4-picolyl) |
| PS | Polystyrene |

-continued

| Abbreviation | Conventional Name |
| --- | --- |
| tBu | tert-butyl |
| tBuOH | tert-butylalcohol |
| TEAClO$_4$ | triethylammonium perchlorate |
| TEAP | triethylammonium phosphate |
| TFA | trifluoroacetic acid |
| TG | Tentagel |
| TIPS | Triisopropylsilane |
| TPP | Triphenylphosphine |
| Trt | trityl [triphenylmethyl, (C$_6$H$_5$)$_3$C-] |

Unless otherwise specified, L-amino acids were used and conventional amino acid terminology is used. Examples of amino acids other than the twenty conventional amino acids include:

| Abbreviation | Conventional Name |
| --- | --- |
| 1-Nal | 1-naphthylalanine |
| 2-Nal | 2-naphthylalanine |
| D-Thi | D-β-(2-thienyl)alanine |
| Cha | β-cyclohexylalanine |
| Aph | β-(4-aminophenyl)alanine |
| D-Cpa | D-β-(4-chlorophenyl)alanine |
| Dip | β,β-diphenylalanine |
| Bip | β-(4,4'-biphenyl)alanine |
| hPhe | homophenylalanine |

-continued

| Abbreviation | Conventional Name |
| --- | --- |
| D-2-Cpa | D-β-(2-chlorophenyl)alanine |
| D-Fpa | D-β-(4-fluorophenyl)alanine |
| D-3-Thi | D-β-(3-thienyl)alanine |
| D-FurAla | D-β-(2-furyl)alanine |
| D-3-Cpa | D-β-(3-chlorophenyl)alanine |
| Nle | Norleucine |
| Hol | homoleucine |
| 2-PhEtHis | N-(2-phenylethyl)histidine |
| 3-MeBuHis | N-(3-methylbutyl)histidine |
| OctHis | N-(n-octyl)histidine |
| EtHis | N-ethylhistidine |

Compounds

According to one embodiment, compounds of the present invention have the general formula I:

$$R^1-(CH_2)_a-NH-CH((CH_2)_b-R^2)-C(O)-NH-CH((CH_2)_c-R^3)-C(O)-Asp-NH-CH((CH_2)_d-R^4)-C(O)-Ser-Phe-Ser-Asp-$$

$$-Glu-NH-CH((CH_2)_e-R^5)-C(O)-NH-CH((CH_2)_f-R^6)-C(O)-Thr-Ile-Leu-Asp-NH-CH((CH_2)_g-R^7)-C(O)-Leu-$$

$$-Ala-NH-CH((CH_2)_h-R^8)-C(O)-Arg-Asp-Phe-Ile-Asn-Trp-Leu-Ile-X_1-Thr-Lys-X_2-X_3-X_4-Z$$

wherein:

$R^1$ is chosen from the group consisting of H, alkyl, aralkyl and aryl;

a is chosen from the group consisting of 0, 1, 2, 3, 4, 5, 6, and 7;

$R^2$ is a heteroaryl;

b is 1 or 2;

$R^3$ and $R^4$ are each independently selected from the group consisting of H and alkyl;

c and d are each independently chosen from the group consisting of 0 and 1;

$R^5$ is chosen from the group consisting of H and alkyl;

e is chosen from the group consisting of 1, 2, 3, and 4;

$R^6$ is chosen from the group consisting of H, alkyl, cycloalkyl, aryl, biaryl, heteroaryl, and —C(O)—$NH_2$;

f is chosen from the group consisting of 0, 1, 2, and 3, with the proviso that if $R^6$ is other than H, f is not 0;

$R^7$ is chosen from the group consisting of alkyl, cycloalkyl, aryl, biaryl, diaryl, heteroaryl and —C(O)—$NH_2$;

g is chosen from the group consisting of 1, 2, and 3;

$R^8$ is chosen from the group consisting of H, alkyl, —CH(OH)—$CH_3$;

h is chosen from the group consisting of 0, 1, 2, and 3;

$X_1$ is Gln or Arg;

$X_2$, $X_3$, and $X_4$ are each independently present or absent and if present, independently selected from the group consisting of Val, Leu, Ile, Ser, Thr, Asp, and Glu;

Z is $NR^9R^{10}$ or OH, wherein:

$R^9$ and $R^{10}$ are each independently selected from the group consisting of hydrogen, alkyl, heteroalkyl, cycloalkyl, aryl, heteroaryl, heteroaralkyl, aralkyl, and —$(CH_2)_x$—[$(CH_2)_2$—O]$_y$—$(CH_2)_x$—[NH—C(O)—$CH_2$—O—$CH_2$]$_z$—C(O)—$NHR^{11}$, wherein:

$R^{11}$ is H or —[$(CH_2)_2$—O]$_y$—$(CH_2)_x$—C(O)—$NH_2$ each x is independently selected from the group consisting of 0, 1, 2, and 3, each y is independently selected from the group consisting of 3, 4, 5, and 6, z is 0 or 1, and $R^9$ and $R^{10}$ are optionally joined to form a 4- to 7-membered ring which may be a heterocycle or a heteroaryl;

and pharmaceutically acceptable salts thereof.

In one embodiment the compound is of formula I wherein $R^6$ and f can not result in L-Asn.

In one embodiment the compound is of formula I wherein $R^7$ and g can not result in L-Asn.

In one embodiment the compound is of formula I wherein $R^5$ and e form Nle.

In one embodiment the compound is of formula I wherein the combination of $R^6$ and f and the combination of $R^7$ and g can not both result in amino acids chosen from the group consisting of Gly, L-Ala, L-Asn, L-Gln, L-Ser, L-Phe, L-Leu, L-Ile, L-Val and L-His.

In one embodiment the compound is of formula I wherein $R^1$ is H, a is 0, $R^2$ is

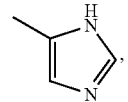

and b is 1. This yields histidine as the first amino acid at the N terminus of the compound.

Alternatively, the compound is of formula I wherein $X_2$, $X_3$, and $X_4$ are all absent.

In another embodiment the compound is of formula I wherein $X_2$, $X_3$, and $X_4$ are all present.

In one embodiment the amino acid formed with the sidechain at $R^6$ is in the D configuration.

In one embodiment the amino acid formed with the side chain at $R^7$ is in the D configuration.

In one embodiment, the compound is example compound 8 of Table 1 wherein amino acid in position 16 is in the D configuration. Alternatively, the compound is compound 12, 13, 29, 30, 32, 35, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, and 70 of Table 1 wherein for each example, the amino acid at position 11 is in the D configuration.

In another embodiment the compound is of formula I wherein Z is $NH_2$ or OH.

In another embodiment the compound is of formula I wherein Z is $NR^9R^{10}$ and one of $R^9$ and $R^{10}$ is hydrogen.

In another embodiment the compound is of formula I wherein c is 0 and $R^3$ is H.

In another embodiment the compound is of formula I wherein e is 3, $R^5$ is methyl, f is 1, $R^6$ is phenyl, g is 1, $R^7$ is isopropyl, $X_2$ is Ile, $X_3$ is Thr, $X_4$ is Asp and Z is $NH_2$ or OH.

In another embodiment the compound is of formula I wherein $R^3$ is hydrogen, c is 0, $R^5$ methyl, e is 3, $R^6$ is phenyl or 2-thienyl, f is 1, $R^7$ phenyl or isopropyl, g is 1, $R^8$ is H or —CH(OH)—$CH_3$ and h is 0 or 1.

In one embodiment the compound is of formula I wherein Z is $NR^9R^{10}$ and $R^9$ is hydrogen and $R^{10}$ is aralkyl or alkyl.

Example compounds of the invention are provided in Table 1. Example compound structures are defined relative to native hGLP-2 which is His-Ala-Asp-Gly-Ser-Phe-Ser-Asp-Glu-Met-Asn-Thr-Ile-Leu-Asp-Asn-Ala-Ala-Arg-Asp-Phe-Ile-Asn-Trp-Leu-Ile-Gln-Thr-Lys-Ile-Thr-Asp (SEQ ID NO:1)

TABLE 1

Example Compounds of the Invention.

| Compound# | Structure | Free Base M.W. |
|---|---|---|
| 1 | [Gly2,D-Ala4,Nle10] hGLP-2 (1-30)-$NH_2$ | 3417.8 |
| 2 | [2-PhEtHis1,Nle10] hGLP-2 (1-30)-$NH_2$ | 3522.0 |
| 3 | [3-MeBuHis1,Nle10] hGLP-2 (1-30)-$NH_2$ | 3487.9 |
| 4 | [OctHis1,Nle10] hGLP-2 (1-30)- $NH_2$ | 3530.0 |
| 5 | [Gly2,Nle10] hGLP-2 (1-30)-NH-i-Am | 3473.8 |
| 6 | [Gly2,Nle10] hGLP-2 (1-30)-NH—Et | 3431.8 |
| 7 | [Gly2,Nle10] hGLP-2 (1-30)-NH-Bzl | 3493.8 |
| 8 | [Gly2,Nle10,D-Phe16] hGLP-2 (1-30)-$NH_2$ | 3436.8 |
| 9 | [Gly2,Nle10,Phe16] hGLP-2 (1-30)-$NH_2$ | 3436.8 |
| 10 | [Gly2,Nle10,Arg28] hGLP-2 (1-30)-NH-i-Am | 3501.9 |
| 11 | [Gly2,Nle10,Leu16] hGLP-2 (1-30)-$NH_2$ | 3402.8 |
| 12 | [Gly2,Nle10,D-Asn11] hGLP-2 (1-30)-NH-i-Am | 3473.9 |
| 13 | [Gly2,Nle10,D-Phe11] hGLP-2 (1-30)-$NH_2$ | 3436.8 |
| 14 | [Gly2,Nle10,Phe11] hGLP-2 (1-30)-$NH_2$ | 3436.8 |
| 15 | [Gly2,Nle10,Leu11] hGLP-2 (1-30)-$NH_2$ | 3402.8 |

TABLE 1-continued

Example Compounds of the Invention.

| Compound# | Structure | Free Base M.W. |
|---|---|---|
| 16 | [Gly2,Nle10,D-Leu11] hGLP-2 (1-30)-NH$_2$ | 3402.8 |
| 17 | [Gly2,Nle10,1-Nal16] hGLP-2 (1-30)-NH$_2$ | 3486.9 |
| 18 | [Gly2,Nle10,Tyr16] hGLP-2 (1-30)-NH$_2$ | 3452.8 |
| 19 | [Gly2,Nle10,His16] hGLP-2 (1-30)-NH$_2$ | 3426.8 |
| 20 | [Gly2,Nle10,2-Nal16] hGLP-2 (1-30)-NH$_2$ | 3486.9 |
| 21 | [Gly2,Nle10,Thi16] hGLP-2 (1-30)-NH$_2$ | 3442.9 |
| 22 | [Gly2,Nle10,Trp16] hGLP-2 (1-30)-NH$_2$ | 3475.9 |
| 23 | [Gly2,Nle10,Cha16] hGLP-2 (1-30)-NH$_2$ | 3442.9 |
| 24 | [Gly2,Nle10,Aph16] hGLP-2 (1-30)-NH$_2$ | 3451.9 |
| 25 | [Gly2,Nle10,Cpa16] hGLP-2 (1-30)-NH$_2$ | 3471.3 |
| 26 | [Gly2,Nle10,Dip16] hGLP-2 (1-30)-NH$_2$ | 3512.9 |
| 27 | [Gly2,Nle10,Bip16] hGLP-2 (1-30)-NH$_2$ | 3512.9 |
| 28 | [Gly2,Nle10,hPhe16] hGLP-2 (1-30)-NH$_2$ | 3450.9 |
| 29 | [Gly2,Nle10,D-Cpa11] hGLP-2 (1-30)-NH$_2$ | 3471.3 |
| 30 | [Gly2,Nle10,D-Trp11] hGLP-2 (1-30)-NH$_2$ | 3475.9 |
| 31 | [Gly2,Nle10,Ile11] hGLP-2 (1-30)-NH$_2$ | 3402.8 |
| 32 | [Gly2,Nle10,D-Thi11] hGLP-2 (1-30)-NH$_2$ | 3442.9 |
| 33 | [Gly2,Nle10,Cpa11] hGLP-2 (1-30)-NH$_2$ | 3471.3 |
| 34 | [Gly2,Nle10,His11] hGLP-2 (1-30)-NH$_2$ | 3426.8 |
| 35 | [Gly2,Nle10,D-His11] hGLP-2 (1-30)-NH$_2$ | 3426.8 |
| 36 | [Gly2,Nle10,Cha11] hGLP-2 (1-30)-NH$_2$ | 3442.9 |
| 37 | [Gly2,Nle10,Hol11] hGLP-2 (1-30)-NH$_2$ | 3416.8 |
| 38 | [Gly2,Nle10,Bip11] hGLP-2 (1-30)-NH$_2$ | 3512.9 |
| 39 | [Gly2,Nle10,D-Tyr11] hGLP-2 (1-30)-NH$_2$ | 3452.8 |
| 40 | [Gly2,Nle10,D-2-Cpa11] hGLP-2 (1-30)-NH$_2$ | 3471.3 |
| 41 | [Gly2,Nle10,D-Fpa11] hGLP-2 (1-30)-NH$_2$ | 3454.8 |
| 42 | [Gly2,Nle10,D-3-Thi11] hGLP-2 (1-30)-NH$_2$ | 3442.9 |
| 43 | [Gly2,Nle10,D-FurAla11] hGLP-2 (1-30)-NH$_2$ | 3426.8 |
| 44 | [Gly2,Nle10,D-3-Cpa11] hGLP-2 (1-30)-NH$_2$ | 3471.3 |
| 45 | [Gly2,Nle10,D-Thi11,Leu16] hGLP-2 (1-30)-NH$_2$ | 3441.9 |
| 46 | [Gly2,Nle10,D-Thi11,Phe16] hGLP-2 (1-30)-NH$_2$ | 3475.9 |
| 47 | [Gly2,Nle10,D-Phe11,Phe16] hGLP-2 (1-30)-NH$_2$ | 3469.9 |
| 48 | [Gly2,Nle10,D-Phe11,Leu16] hGLP-2 (1-30)-NH$_2$ | 3435.9 |
| 49 | [Gly2,Nle10,D-Phe11,Tyr16] hGLP-2 (1-30)-NH$_2$ | 3485.9 |
| 50 | [Gly2,Nle10,D-Thi11,Tyr16] hGLP-2 (1-30)-NH$_2$ | 3491.9 |
| 51 | [Gly2,Nle10,D-Phe11,Leu16] hGLP-2 (1-33)-NH$_2$ | 3765.3 |
| 52 | [Gly2,Nle10,D-Phe11,Leu16,Thr19] hGLP-2(1-30)-NH$_2$ | 3465.9 |
| 53 | [Gly2,Nle10,D-Phe11,Leu16] hGLP-2(1-33)-NHEt | 3793.3 |
| 54 | [Gly2,Nle10,D-Phe11,Leu16] hGLP-2(1-33)-NH-4-Pic | 3856.3 |
| 55 | [Gly2,Nle10,D-Phe11,Leu16] hGLP-2(1-33)-NH—((CH$_2$)$_2$O)$_4$—(CH$_2$)$_2$—C(O)—NH$_2$ | 4012.5 |
| 56 | [Gly2,Nle10,D-Phe11,Leu16] hGLP-2(1-33)-NH—CH$_2$—((CH$_2$)$_2$O)$_3$—(CH$_2$)$_3$—NHC(O)—CH$_2$—O—CH$_2$—C(O)—NH$_2$ | 4083.6 |
| 57 | [Gly2,Nle10,D-Phe11,Leu16] hGLP-2(1-33)-NH-isobutyl | 3821.3 |
| 58 | [Gly2,Nle10,D-Phe11,Leu16] hGLP-2(1-33)-NH-Benzyl | 3855.3 |
| 59 | [Gly2,Nle10,D-Phe11,Leu16] hGLP-2(1-33)-OH | 3766.2 |
| 60 | [Gly2,Nle10,D-Phe11,Phe16] hGLP-2(1-33)-NH—CH$_2$—((CH$_2$)$_2$O)$_3$—(CH$_2$)$_3$—NH—C(O)—CH$_2$—O—CH$_2$—C(O)—NH$_2$ | 4134.6 |
| 61 | [Gly2,Nle10,D-Phe11,Phe16] hGLP-2(1-33)-NH—CH$_2$—((CH$_2$)$_2$O)$_3$—(CH$_2$)$_3$—NH—C(O)—CH$_2$—O—CH$_2$—C(O)—NH—((CH$_2$)$_2$O)$_6$—(CH$_2$)$_2$—C(O)—NH$_2$ | 4453.0 |
| 62 | [Gly2,Nle10,D-Thi11,Leu16,Thr19] hGLP-2(1-33)-NH$_2$ | 3805.3 |
| 63 | [Gly2,Nle10,D-Phe11,Phe16] hGLP-2(1-33)-NH$_2$ | 3799.2 |
| 64 | [Gly2,Nle10,D-Phe11,Phe16] hGLP-2(1-33)-OH | 3800.2 |
| 65 | [Gly2,Nle10,D-3-Cpa11,2-Nal16] hGLP-2(1-33)-NH$_2$ | 3883.7 |
| 66 | [Gly2,Nle10,D-3-Cpa11,Phe16] hGLP-2(1-33)-NH$_2$ | 3833.7 |
| 67 | [Gly2,Nle10,D-3-Cpa11,Leu16] hGLP-2(1-33)-NH$_2$ | 3799.6 |
| 68 | [Gly2,Nle10,D-Thi11,Phe16] hGLP-2(1-33)-NH$_2$ | 3805.2 |
| 69 | [Gly2,D-Ala4,Nle10,D-Phe11,Leu16] hGLP-2(1-33)-NH$_2$ | 3779.3 |
| 70 | [EtHis1,D-Ala4,Nle10,D-Phe11,Leu16] hGLP-2(1-33)-NH$_2$ | 3821.4 |

TABLE 2

Key to Amino Acid Nomenclature.

| Amino Acid | Position | Claim Nomenclature |
|---|---|---|
| 2-PhEtHis | 1 | $R^1$ = (phenyl), $R^2$ = (5-methylimidazole), a = 2, b = 1 |
| 3-MeBuHis | 1 | $R^1$ = —CH(CH$_3$)$_2$, $R^2$ = (5-methylimidazole), a = 2, b = 1 |

TABLE 2-continued

Key to Amino Acid Nomenclature.

| Amino Acid | Position | Claim Nomenclature | |
|---|---|---|---|
| OctHis | 1 | $R^1 = $ —CH$_3$, $R^2 = $ 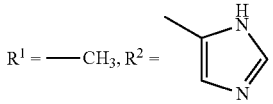 | a = 7, b = 1 |
| EtHis | 1 | $R^1 = $ —CH$_3$, $R^2 = $ 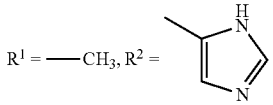 | a = 1, b = 1 |
| Gly | 2 | $R^3 = $ H | c = 0 |
| D-Ala | 4 | $R^4 = $ H | d = 1 |
| Nle | 10 | $R^5 = $ —CH$_3$ | e = 3 |
| D-Asn | 11 | $R^6 = $ —C(O)—NH$_2$ | f = 1 |
| D-Phe | 11 | $R^6 = $ 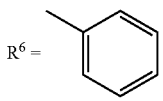 | f = 1 |
| Phe | 11 | $R^6 = $ 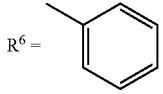 | f = 1 |
| Leu | 11 | $R^6 = $ —CH(CH$_3$)$_2$ | f = 1 |
| D-Leu | 11 | $R^6 = $ —CH(CH$_3$)$_2$ | f = 1 |
| Cpa | 11 | $R^6 = $ 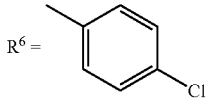 | f = 1 |
| D-Cpa | 11 | $R^6 = $ 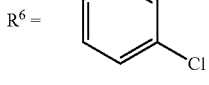 | f = 1 |
| D-2-Cpa | 11 | $R^6 = $ 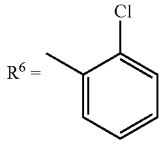 | f = 1 |
| D-3-Cpa | 11 | $R^6 = $ 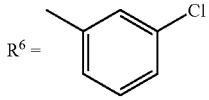 | f = 1 |
| D-Fpa | 11 | $R^6 = $ 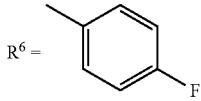 | f = 1 |
| D-Trp | 11 | $R^6 = $ 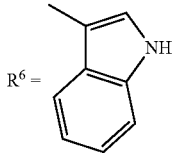 | f = 1 |
| Ile | 11 | $R^6 = $ —CH(CH$_3$)—CH$_2$—CH$_3$ | f = 0 |
| D-Thi | 11 | $R^6 = $ 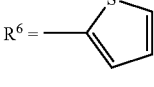 | f = 1 |
| D-3-Thi | 11 | $R^6 = $ 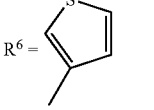 | f = 1 |
| His | 11 | $R^6 = $ 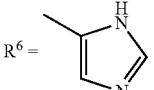 | f = 1 |
| D-His | 11 | $R^6 = $ 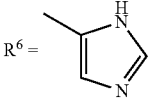 | f = 1 |
| Cha | 11 | $R^6 = $ 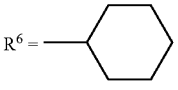 | f = 1 |
| Hol | 11 | $R^6 = $ —CH(CH$_3$)$_2$ | f = 2 |
| Bip | 11 | $R^6 = $ 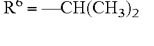 | f = 1 |
| D-Tyr | 11 | $R^6 = $ 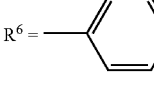 | f = 1 |
| D-FurAla | 11 | $R^6 = $ 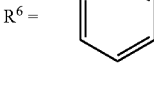 | f = 1 |
| D-Phe | 16 | $R^7 = $ 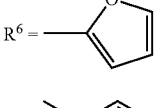 | g = 1 |
| Phe | 16 | $R^7 = $ 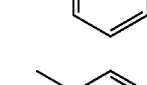 | g = 1 |
| hPhe | 16 | $R^7 = $ 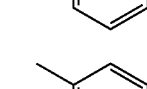 | g = 2 |
| Leu | 16 | $R^7 = $ —CH(CH$_3$)$_2$ | g = 1 |
| 1-Nal | 16 | $R^7 = $ 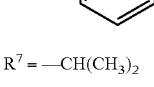 | g = 1 |

TABLE 2-continued

Key to Amino Acid Nomenclature.

| Amino Acid | Position | Claim Nomenclature | |
|---|---|---|---|
| 2-Nal | 16 | $R^7 =$ 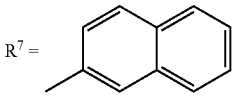 | g = 1 |
| Tyr | 16 | $R^7 =$ 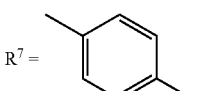 | g = 1 |
| His | 16 | $R^7 =$ 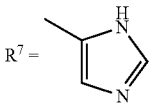 | g = 1 |
| Thi | 16 | $R^7 =$ 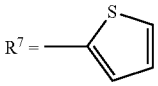 | g = 1 |
| Trp | 16 | $R^7 =$ 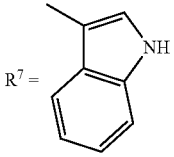 | g = 1 |
| Cha | 16 | $R^7 =$ 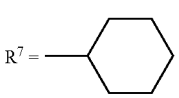 | g = 1 |
| Aph | 16 | $R^7 =$ 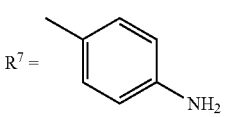 | g = 1 |
| Cpa | 16 | $R^7 =$ 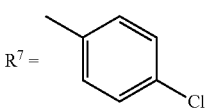 | g = 1 |
| Dip | 16 | $R^7 =$ 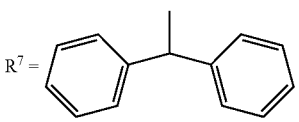 | g = 0 |
| Bip | 16 | $R^7 =$ 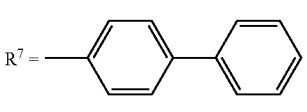 | g = 1 |
| Thr | 19 | $R^8 =$ —CH(OH)—CH$_3$ | h = 0 |

Synthesis

α-Amino acid derivatives were purchased from commercial providers (Bachem, Novabiochem and Peptides International). Resins were purchased from commercial providers (Applied Biosystems and Novabiochem). All additional reagents, chemicals and solvents were purchased from Sigma-Aldrich, Fluka and Acros Organics.

The compounds herein were synthesised by standard methods in solid phase peptide chemistry utilising Fmoc methodology and an Applied Biosystems Pioneer 'Peptide Synthesis System' continuous-flow automated peptide synthesizer or an Applied Biosystems 433A automated peptide synthesizer with cycle protocols specified by Applied Biosystems.

Preparative HPLC was performed on a Waters Delta Prep LC 4000 using a PrepPack cartridge Delta-Pack C18, 300 Å, 15 μm, 47×300 mm at a flow rate of 100 ml/min. Analytical reverse phase HPLC was performed on a Waters 600 liquid chromatograph using a Vydac column 218TP54, C18 (5 μm, 4.6×250 mm) at a flow rate of 2 ml/min. Final compound analysis was performed on an Agilent Technologies 1200 Series chromatograph by reverse phase HPLC on a Phenomenex MAX-RP 80 Å C18 column (4 μm, 2×150 mm) at a flow rate of 0.3 ml/min. Mass spectra were recorded on a MAT Finnigan LCQ electrospray mass spectrometer. Results of the final compound analysis is provided for the example compounds in Table 1.

Unless otherwise provided, all reactions were performed at room temperature. The following standard reference literature provides further guidance on general experimental set up, as well as on the availability of required starting material and reagents: Kates, S. A., Albericio, F., Eds., *Solid Phase Synthesis: A Practical Guide*, Marcel Dekker, New York, Basel, 2000; Greene, T. W., Wuts, P. G. M., *Protective Groups in Organic Synthesis*, John Wiley Sons Inc., 2$^{nd}$ Edition, 1991; Stewart, J. M., Young, J. D., *Solid Phase Synthesis*, Pierce Chemical Company, 1984; Bisello, et al., *J. Biol. Chem.* 1998, 273, 22498-22505; Merrifield, *J. Am. Chem. Soc.* 1963, 85, 2149-2154; and Chang and White P. D., '*Fmoc Solid Phase Peptide Synthesis: a Practical Approach*', Oxford University Press, Oxford, 2000.

N-α-Fmoc-Pal-PEG-PS resin (Applied Biosystems, Foster City, Calif.) was used as starting material for C-terminal primary carboxylamide peptides. N-α-Fmoc protected amino acid attached to NovaSyn® TGT resin (Novabiochem, San Diego, Calif.) was used as starting material for peptides with a free carboxyl C-terminus.

The following protecting groups were utilized to protect the given amino acid side chain functional groups: 2,2,4,6,7-pentamethyldihydrobenzofuran-5-sulfonyl (Arg); t-butyl group (Glu, Asp, Ser, Thr and Tyr); trityl group (His, Gln and Asn); t-butoxycarbonyl group (Lys and Trp).

All coupling of Fmoc-protected amino acids were mediated with HATU/DIPEA in DMF. Single couplings of 35-50 minutes with a 4-fold excess of activated Fmoc-protected amino acids were used during the synthesis. Removal of the Fmoc protecting group was performed by a six minute flow-wash of the peptide resin with 30% piperidine in DMF on Pioneer or 20% piperidine/NMP with UV monitoring on the ABI 433A synthesizer.

Peptide analogs where a=0 and $R^1$=H were assembled automatically on the resin until the position 5 residue has been coupled. The N-terminal Fmoc protecting group was then removed and the (1-4) fragment was manually introduced with 2 equivalents of a fully protected N$^α$-Boc-tetrapeptide carboxylic acid in a single coupling mediated by DIC/HOBt in DMF. The tetrapeptide was prepared separately by manual synthesis on H-Gly-2-Cl-Trityl resin (Novabiochem).

Peptide analogs where a≠0 or, if a=0, then $R^1$≠H and d=0 and $R^4$=H were assembled automatically on the resin until the position 4 Gly residue has been coupled. The Gly residue was introduced with Hmb (2-hydroxy-4-methoxybenzyl) backbone protecting group as Fmoc-Hmb(Fmoc)Gly-OH. The N-terminal Fmoc protecting groups were removed and Fmoc-Asp(OtBu)-OH (5 equivalents) was coupled manually utilizing DIC in DCM. The two remaining residues were introduced manually using 4 equivalents of Fmoc-protected amino acids/DIC/HOBt in DMF. The N-terminal Fmoc group was replaced with the 2-nitrobenzenesulfonyl group and the resin-bound sulfonamide was alkylated with an appropriate primary alcohol under the Mitsunobu reaction conditions (10 equivalents of alcohol/TPP/DIAD in DME, overnight). The 2-nitrobenzenesulfonyl group was then removed with 5% potassium thiophenolate in DMF.

Upon completion of the peptide synthesis, the peptides were washed with DCM and dried in vacuo. The peptides were treated with TFA/H$_2$O/TIPS 44:3:2 (v/v/v, 25 ml) for 2 h in order to remove the side-chain protecting groups with concomitant cleavage of the peptide from the resin. The peptide was filtered, precipitated with cool t-butylmethylether, centrifuged (the solid was retained), washed with t-butylmethylether, re-dissolved in acetonitrile-H$_2$O (70:30), lyophilised and purified by preparative HPLC.

Purification of the peptides was performed with preparative HPLC. Each crude peptide was purified with either buffer system P or buffer system C, or P followed by C. The fractions with a purity exceeding 93%, determined by reverse-phase analytical HPLC, were pooled and reloaded onto the column and eluted with buffer T to provide trifluoroacetate salts. To obtain acetate salts the fractions from runs with buffer P or C were reloaded onto the column and the column was washed with 5 volumes of 0.1 M ammonium acetate. The final product was eluted with buffer A. The fractions were pooled and lyophilized.

TABLE 3

Buffer Compositions

| Buffer | Component A | Component B |
| --- | --- | --- |
| P | 0.25M Triethylammonium Phosphate (TEAP) (pH 2.3 or pH 7.0) | 60% acetonitrile, 40% Component A |
| C | 0.1M Triethylammonium Perchlorate (TEAClO$_4$) (pH 2.3) | 65% acetonitrile, 35% Component A |
| T | 0.1% Trifluoroacetic acid (TFA) | 60% acetonitrile, 0.1% TFA |
| A | 2% Acetic acid (AcOH) | 60% acetonitrile, 2% AcOH |

Additional Syntheses

To synthesize the C-terminal secondary/tertiary carboxylamide peptides (wherein at least one of R$^9$ or R$^{10}$ is not H), the fully protected C-terminal carboxylic acid peptides were cleaved from NovaSyn® TGT resin with the HIPF/DCM 1/4 (v/v) cocktail and were subsequently coupled in solution with a proper amine using DIC/HOAt in dry the chloroform/2,2,2-trifluoroethanol 3/1 (v/v) solvent system. The protecting groups were subsequently removed with the TFA/H$_2$O/TIPS 44:3:2 (v/v/v) cocktail and the analogs were purified by preparative HPLC. Methods are well known in the art, for example as described in M. Goodman, A. Felix, L. Moroder, C. Toniolo, Editors; *Synthesis of Peptides and Peptidomimetics*, Houben-Weyl, Vols E22a to E22e, Georg Thime Verlag, 2004.

In another embodiment, secondary amides, such as compounds of the present invention wherein R$^9$ is hydrogen and R$^{10}$ is not hydrogen, may be made on solid phase as described in "Backbone Amide Linker (BAL) Strategy for Solid-Phase Synthesis of C-Terminal-Modified and Cyclic Peptides," Knud J. Jensen, Jordi Alsina, Michael F. Songster, Josef Vagner, Fernando Albericio, and George Barany, *Journal of the American Chemical Society* 1998 120 (22), 5441-5452 and "An Alkanesulfonamide "Safety-Catch" Linker for Solid-Phase Synthesis," Bradley J. Backes and Jonathan A. Ellman, *The Journal of Organic Chemistry* 1999 64 (7), 2322-2330.

In yet another embodiment, tertiary or cyclic amides, such as compounds of the present invention where in neither R$^9$ nor R$^{10}$ are hydrogen and R$^9$ and R$^{10}$ are optionally joined to form a ring, may be made on solid phase as described in "Structure-Based Design and Synthesis of High Affinity Tripeptide Ligands of the Grb2-SH2 Domain," Pascal Furet, Brigitte Gay, Giorgio Caravatti, Carlos García-Echeverría, Joseph Rahuel, Joseph Schoepfer, and Heinz Fretz, *Journal of Medicinal Chemistry* 1998 41 (18), 3442-3449.

GLP-2 Receptor Agonist Activity

Agonist activities of compounds of the invention on the hGLP-2 receptor were determined in a transcriptional reporter gene assay by transiently transfecting an hGLP-2 receptor expression DNA into a Human Embryonic Kidney (HEK-293) cell line in concert with a reporter DNA containing intracellular cAMP responsive promoter elements regulating expression of firefly luciferase. See for example Himmler et al., *J. Recept. Res.*, (1993), 13, 79-74 for further guidance on this assay. Cells were exposed to serial dilutions of compounds diluted half-log per dose for 5 hours, followed by lysis of cells, determination of luciferase activity, and determination of compound efficacies and EC$_{50}$ values through non-linear regression. hGLP-2, the 33-amino acid endogenous ligand was used as an internal control in each experiment. The data displayed normal variation in individual assays performed.

The in vitro assay results (EC$_{50}$ value for hGLP-2 receptor potency as the geometric mean expressed in nanomol/l (nM)) for the compounds of Table 1 were in the range of from about 0.01 nM to about 1 nM. Each compound tested was similar in potency or more potent at the hGLP-2 receptor than the endogenous ligand in these assays.

The foregoing results indicate that compounds disclosed herein are within the scope of the invention and may for instance be useful in the safe and efficacious treatment of human beings.

Pharmacokinetics

Pharmacokinetic (PK) parameters of illustrative agonists of the GLP-2 receptor were determined in adult male Sprague-Dawley rats post intravenous bolus injection of compounds at doses of 0.1-1.0 mg/kg. Three or four doubly cannulated animals per compound were dosed via jugular vein, blood samples were collected at several intervals via carotid artery, and plasma samples were prepared from whole blood using K$_2$EDTA as anticoagulant. Subsequent bioanalysis of samples included compound extraction and plasma concentration determination using standard LC/MS/MS methods. Analyte concentration was calculated from internal standard normalized peak area and calibration curves.

For calculation of PK parameters the compound concentration-time curves were analyzed with the noncompartmental data analysis software package PK Solutions 2.0™ (Summit Research Services, Montrose Colo.). The systemic clearance per kg body weight (CL) was calculated as the dose per kg body weight divided by the AUC extrapolated to infinity based on trapezoid calculation (AUC∞). Values reported are the arithmetic mean and standard deviation from the number of animals used for each compound as indicated on Table 3.

Each compound tested was similar in clearance or exhibited a markedly lower clearance than hGLP-2 and teduglutide. Data from tested compounds are shown in Table 3.

TABLE 4

PK Data

| | | CL (ml/kg/min) | | |
|---|---|---|---|---|
| Cpd. # | Dose (mg FB/kg) | Average | Standard Deviation | n |
| 1 | 0.20 | 7.1 | 0.7 | 4 |
| 5 | 0.20 | 1.2 | 0.1 | 3 |
| 6 | 0.20 | 6.3 | 1.0 | 3 |
| 10 | 0.18 | 1.5 | 0.2 | 3 |
| 11 | 0.20 | 0.84 | 0.06 | 3 |
| 13 | 0.20 | 1.2 | 0.0 | 3 |
| 15 | 0.20 | 2.8 | 0.1 | 3 |
| 16 | 0.20 | 3.3 | 0.4 | 3 |
| 17 | 0.20 | 0.43 | 0.03 | 3 |
| 18 | 0.20 | 1.2 | 0.1 | 3 |
| 20 | 0.18 | 0.28 | 0.05 | 3 |
| 22 | 0.20 | 0.50 | 0.02 | 3 |
| 23 | 0.20 | 0.41 | 0.05 | 3 |
| 24 | 0.20 | 1.9 | 0.1 | 3 |
| 26 | 0.20 | 0.33 | 0.03 | 3 |
| 28 | 0.20 | 0.44 | 0.04 | 3 |
| 29 | 0.20 | 0.51 | 0.02 | 3 |
| 30 | 0.20 | 1.2 | 0.1 | 3 |
| 31 | 0.18 | 5.6 | 0.2 | 3 |
| 32 | 0.20 | 1.1 | 0.1 | 3 |
| 39 | 0.20 | 4.9 | 0.2 | 3 |
| 40 | 0.20 | 0.73 | 0.09 | 3 |
| 42 | 0.20 | 1.3 | 0.1 | 3 |
| 44 | 0.20 | 0.32 | 0.02 | 3 |
| 45 | 0.20 | 0.33 | 0.03 | 3 |
| 46 | 0.20 | 0.26 | 0.02 | 3 |
| 47 | 0.20 | 0.30 | 0.03 | 3 |
| 48 | 0.20 | 0.37 | 0.04 | 3 |
| 49 | 0.20 | 0.48 | 0.07 | 3 |
| 50 | 0.20 | 0.52 | 0.07 | 3 |
| 51 | 0.20 | 0.27 | 0.04 | 3 |
| 51 | 0.10 | 0.20 | 0.02 | 3 |
| 52 | 0.20 | 0.49 | 0.04 | 3 |
| 53 | 0.20 | 0.19 | 0.02 | 3 |
| 54 | 0.20 | 0.27 | 0.01 | 3 |
| 55 | 0.20 | 0.23 | 0.03 | 3 |
| 56 | 0.20 | 0.28 | 0.01 | 3 |
| 57 | 0.20 | 0.17 | 0.01 | 3 |
| 58 | 0.20 | 0.10 | 0.01 | 3 |
| 59 | 0.20 | 0.22 | 0.07 | 7 |
| 60 | 0.20 | 0.29 | 0.02 | 3 |
| 61 | 0.20 | 0.16 | 0.04 | 3 |
| 62 | 0.20 | 0.28 | 0.03 | 3 |
| 63 | 0.20 | 0.24 | 0.02 | 3 |
| 64 | 0.20 | 0.15 | 0.03 | 3 |
| 66 | 0.20 | 0.12 | 0.01 | 3 |
| 68 | 0.20 | 0.15 | 0.03 | 3 |
| hGLP-2 | 1.0 | 24.6 | 2.3 | 4 |
| teduglutide | 1.0 | 8.0 | 0.3 | 4 |
| teduglutide | 0.20 | 9.9 | 2.1 | 15 |
| ZP-1846 | 0.20 | 2.8 | 0.4 | 3 |
| ZP-1848 | 0.20 | 2.4 | 0.4 | 3 |

Pharmaceutical Compositions

According to the present invention in a further aspect there is provided the use of a compound of formula (I), as defined herein, as a pharmaceutical.

According to the present invention in a further aspect there is provided a pharmaceutical composition comprising a compound of formula (I), as defined herein, as active ingredient in association with a pharmaceutically acceptable adjuvant, diluent or carrier.

The pharmaceutical composition may be adapted for oral, intravenous, topical, intraperitoneal, nasal, buccal, intraocular, intra-aural, sublingual, intramuscular and subcutaneous administration and for administration via the respiratory tract e.g. in the form of an aerosol or an air-suspended fine powder. The composition may thus for instance be in the form of tablets, capsules, powders, microparticles, granules, syrups, suspensions, solutions, transdermal patches or suppositories.

It should be noted that the pharmaceutical composition according to the present invention may include two or more of the above defined compounds.

The pharmaceutical composition may optionally comprise e.g. at least one further additive selected from a disintegrating agent, binder, lubricant, flavouring agent, preservative, colourant and any mixture thereof. Examples of such and other additives are found in 'Handbook of Pharmaceutical Excipients'; Ed. A. H. Kibbe, $3^{rd}$ Ed., American Pharmaceutical Association, USA and Pharmaceutical Press UK, 2000.

The pharmaceutical composition may be adapted for parenteral administration, e.g. by injection. Formulations suitable for parenteral administration include aqueous and non-aqueous, isotonic sterile injection solutions, which can contain antioxidants, buffers, bacteriostatics, and solutes that render the formulation isotonic with the blood of the intended recipient, and aqueous and non-aqueous sterile suspensions that can include suspending agents, solubilizers, thickening agents, stabilizers, and preservatives. Liquid carriers, for injectable solutions, include by way of example and without limitation water, saline, aqueous dextrose and glycols. Examples of parenteral formulations can be found in Avis K., Lieberman H., and Lachman L., Editors, *Pharmaceutical Dosage Forms: Parenteral Medications Volume* 1, Marcel Dekker, New York, 1992. Examples of suspension formulations can be found in Burgess, D. J. Ed., *Injectable Dispersed Systems—Formulation, Processing, and Performance*, Informa Healthcare, New York, 2007.

In a further aspect the present invention provides the use of a compound as outlined above for the manufacture of a medicament for treatment of diseases including gastrointestinal injury, diarrheal diseases, intestinal insufficiency, acid-induced intestinal injury, arginine deficiency, idiopathic hypospermia, obesity, celiac disease, catabolic illness, chemotherapy-induced enteritis, febrile neutropenia, diabetes, obesity, fat malabsorption, steatorrhea, autoimmune diseases, food allergies, gastric ulcers, hypoglycemia, gastrointestinal barrier disorders, sepsis, bacterial peritonitis, burn-induced intestinal damage, decreased gastrointestinal motility, inflammatory bowel disease, intestinal failure, chemotherapy-associated bacteremia, bowel trauma, bowel ischemia, mesenteric ischemia, irritable bowel syndrome, short bowel syndrome, malnutrition, necrotizing enterocolitis, necrotizing pancreatitis, neonatal feeding intolerance, NSAID-induced gastrointestinal damage, nutritional insufficiency, total parenteral nutrition damage to gastrointestinal tract, neonatal nutritional insufficiency, radiation-induced enteritis, radiation-induced injury to the intestines, mucositis, pouchitis, ischemia, stroke, depression, autism, osteoporosis, and traumatic brain injury. Inflammatory bowel disease includes, but is not limited to, Crohn's Disease and ulcerative colitis.

In a further aspect the present invention provides the use of a compound as outlined above for the manufacture of a medicament for regulating appetite; enhancing, stimulating or accelerating weight loss; enhancing, stimulating or accelerating gastric relaxation; controlling glucose levels; enhancing, stimulating or accelerating hunger satiety; enhancing intestinal immune function; enhancing, stimulating or accelerating intestinal wound healing; enhancing, stimulating or accelerating juvenile weight loss; enhancing, stimulating or accelerating weight loss; enhancing, stimulating or accelerating neonatal bowel development; enhancing, stimulating or accelerating fetal or neonatal development; preventing intestinal cancers; enhancing or stimulating mucosal integrity; minimizing, mitigating, or preventing bacterial translocation in the intestines; enhancing, stimulating or accelerating recovery of the intestines after surgery; preventing relapses of inflammatory bowel disease, including Crohn's Disease and ulcerative colitis, e.g. after surgery; achieving, maintaining energy homeostasis; enhancing, stimulating or accelerating astroglial regeneration; or enhancing, stimulating or accelerating repair or growth of the central nervous system.

In another aspect the invention provides methods for treatment of diseases including gastrointestinal injury, diarrheal diseases, intestinal insufficiency, acid-induced intestinal injury, arginine deficiency, idiopathic hypospermia, obesity, celiac disease, catabolic illness, chemotherapy-induced enteritis, febrile neutropenia, diabetes, obesity, fat malabsorption, steatorrhea, autoimmune diseases, food allergies, gastric ulcers, hypoglycemia, gastrointestinal barrier disorders, sepsis, bacterial peritonitis, burn-induced intestinal damage, decreased gastrointestinal motility, inflammatory bowel disease, intestinal failure, chemotherapy-associated bacteremia, bowel trauma, bowel ischemia, mesenteric ischemia, irritable bowel syndrome, short bowel syndrome, malnutrition, necrotizing enterocolitis, necrotizing pancreatitis, neonatal feeding intolerance, NSAID-induced gastrointestinal damage, nutritional insufficiency, total parenteral nutrition damage to gastrointestinal tract, neonatal nutritional insufficiency, radiation-induced enteritis, radiation-induced injury to the intestines, mucositis, pouchitis, ischemia, stroke, depression, autism, osteoporosis, and traumatic brain injury, wherein said method comprises administering to an animal, including human, patient a therapeutically effective amount of a compound as outlined above. Inflammatory bowel disease includes, but is not limited to, Crohn's Disease and ulcerative colitis.

In another aspect the invention provides methods for regulating appetite; enhancing, stimulating or accelerating weight loss; enhancing, stimulating or accelerating gastric relaxation; controlling glucose levels; enhancing, stimulating or accelerating hunger satiety; enhancing intestinal immune function; enhancing, stimulating or accelerating intestinal wound healing; enhancing, stimulating or accelerating juvenile weight loss; enhancing, stimulating or accelerating weight loss; enhancing, stimulating or accelerating neonatal bowel development; enhancing, stimulating or accelerating fetal or neonatal development; preventing intestinal cancers; enhancing or stimulating mucosal integrity; minimizing, mitigating, or preventing bacterial translocation in the intestines; enhancing, stimulating or accelerating recovery of the intestines after surgery; preventing relapses of inflammatory bowel disease, including Crohn's Disease and ulcerative colitis, e.g. after surgery; achieving, maintaining energy homeostasis; enhancing, stimulating or accelerating astroglial regeneration; or enhancing, stimulating or accelerating repair or growth of the central nervous system, wherein said method comprises administering to an animal, including human, patient a therapeutically effective amount of a compound as outlined above.

As used herein 'treatment' means the alleviation of symptoms, postponement of the onset of the disease and/or the cure of the disease when a compound of the invention is administered in a suitable dose.

The typical dosage of the compounds according to the present invention varies within a wide range and will depend on various factors such as the individual needs of each patient and the route of administration. The dosage may be administered once daily or more frequently than once daily, e.g. intermittently. The dosage administered, for example, is generally within the range of 0.01-5000 μg, e.g. from 100 to 2000 μg per day, e.g. by subcutaneous injection. A physician of ordinary skill in the art will be able to optimize the dosage to the situation at hand.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

We claim:

1. A compound of formula I:

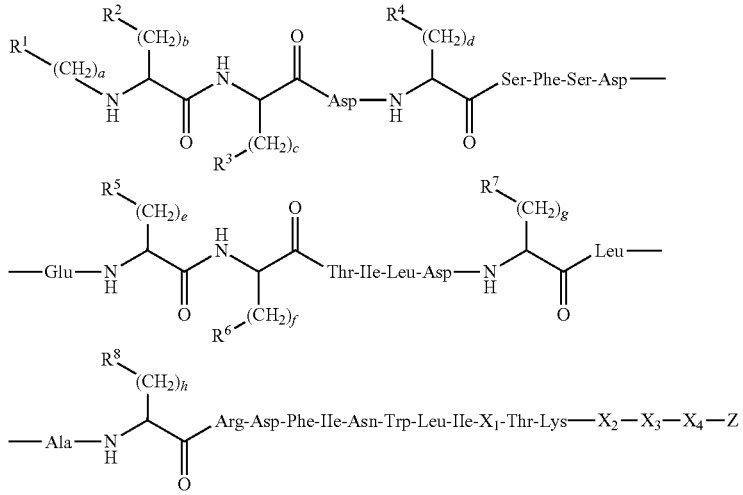

wherein:
- $R^1$ is chosen from the group consisting of H, alkyl, aralkyl and aryl;
- a is chosen from the group consisting of 0, 1, 2, 3, 4, 5, 6, and 7;
- $R^2$ is a heteroaryl;
- b is 1 or 2;
- $R^3$ and $R^4$ are each independently selected from the group consisting of H and alkyl;
- c and d are each independently chosen from the group consisting of 0 and 1;
- $R^5$ is chosen from the group consisting of, H and alkyl;
- e is chosen from the group consisting of 1, 2, 3, and 4;
- $R^6$ is chosen from the group consisting of H, alkyl, cycloalkyl, aryl, biaryl, heteroaryl, and —C(O)—NH$_2$, wherein the amino acid of which $R^6$ is a part is in the D configuration;
- f is chosen from the group consisting of 0, 1, 2, and 3, with the proviso that if $R^6$ is other than H, f is not 0;
- $R^7$ is chosen from the group consisting of alkyl, cycloalkyl, aryl, biaryl, diaryl, heteroaryl and —C(O)—NH$_2$;
- g is chosen from the group consisting of 1, 2, and 3;
- $R^8$ is chosen from the group consisting of H, alkyl, —CH(OH)—CH$_3$;
- h is chosen from the group consisting of 0, 1, 2, and 3;
- $X_1$ is Gln or Arg;
- $X_2$, $X_3$, and $X_4$ are each independently present or absent and if present, independently selected from the group consisting of Val, Leu, Ile, Ser, Thr, Asp, and Glu;
- Z is NR$^9$R$^{10}$ or OH, wherein:
  - $R^9$ and $R^{10}$ are each independently selected from the group consisting of hydrogen, alkyl, heteroalkyl, cycloalkyl, aryl, heteroaryl, heteroaralkyl, aralkyl, and
  - (CH$_2$)$_x$—[(CH$_2$)$_2$—O]$_y$—(CH$_2$)$_x$—[NH—C(O)—CH$_2$—O—CH$_2$]$_z$—C(O)—NHR$^{11}$, wherein:
    - $R^{11}$ is H or —[(CH$_2$)$_2$—O]$_y$—(CH$_2$)$_x$—C(O)—NH$_2$
    - each x is independently selected from the group consisting of 0, 1, 2, and 3,
    - each y is independently selected from the group consisting of 3, 4, 5, and 6,
    - z is 0 or 1, and
    - $R^9$ and $R^{10}$ are optionally joined to form a 4- to 7-membered ring which may be a heterocycle or a heteroaryl;

and pharmaceutically acceptable salts thereof.

2. The compound of claim 1 wherein $R^7$ and g can not result in L-Asn.

3. The compound of claim 1 wherein $R^5$ and e form Nle.

4. The compound of claim 1 wherein $R^1$ is H, a is 0, $R^2$ is

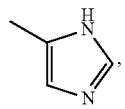

and b is 1.

5. The compound of claim 1 wherein $X_2$, $X_3$, and $X_4$ are all absent.

6. The compound of claim 1 wherein $X_2$, $X_3$, and $X_4$ are all present.

7. The compound of claim 1 wherein Z is $NH_2$ or OH.

8. The compound of claim 1 wherein Z is $NR^9R^{10}$ and one of $R^9$ and $R^{10}$ is hydrogen.

9. The compound of claim 1 wherein c is 0 and $R^3$ is H.

10. The compound of claim 1 wherein e is 3, $R^5$ is methyl, f is 1, $R^6$ is phenyl, g is 1, $R^7$ is isopropyl, $X_2$ is Ile, $X_3$ is Thr, $X_4$ is Asp and Z is $NH_2$ or OH.

11. The compound of claim 1 wherein $R^3$ is hydrogen, c is 0, $R^5$ methyl, e is 3, $R^6$ is phenyl or 2-thienyl, f is 1, $R^7$ phenyl or isopropyl, g is 1, $R^8$ is H or —CH(OH)—CH$_3$ and h is 0 or 1.

12. The compound of claim 1 selected from the group consisting of:
    His-Gly-Asp-Gly-Ser-Phe-Ser-Asp-Glu-Nle-D-Thi-Thr-Ile-Leu-Asp-Phe-Leu-Ala-Ala-Arg-Asp-Phe-Ile-Asn-Trp-Leu-Ile-Gln-Thr-Lys-NH$_2$,
    His-Gly-Asp-Gly-Ser-Phe-Ser-Asp-Glu-Nle-D-Phe-Thr-Ile-Leu-Asp-Phe-Leu-Ala-Ala-Arg-Asp-Phe-Ile-Asn-Trp-Leu-Ile-Gln-Thr-Lys-NH$_2$,
    His-Gly-Asp-Gly-Ser-Phe-Ser-Asp-Glu-Nle-D-Phe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-N H$_2$,
    His-Gly-Asp-Gly-Ser-Phe-Ser-Asp-Glu-Nle-D-Phe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-NHEt,
    His-Gly-Asp-Gly-Ser-Phe-Ser-Asp-Glu-Nle-D-Phe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-NH-4-Pic,
    His-Gly-Asp-Gly-Ser-Phe-Ser-Asp-Glu-Nle-D-Phe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-NH—((CH$_2$)$_2$O)$_4$—(CH$_2$)$_2$—CO—NH$_2$,
    His-Gly-Asp-Gly-Ser-Phe-Ser-Asp-Glu-Nle-D-Phe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-NH—CH$_2$—((CH$_2$)$_2$O)$_3$—(CH$_2$)$_3$—NHCO—CH$_2$—O—CH$_2$—CO—NH$_2$, and
    His-Gly-Asp-Gly-Ser-Phe-Ser-Asp-Glu-Nle-D-Phe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-NH-isobutyl.

13. The compound of claim 1 selected from the group consisting of:
    His-Gly-Asp-Gly-Ser-Phe-Ser-Asp-Glu-Nle-D-Phe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-OH,
    His-Gly-Asp-Gly-Ser-Phe-Ser-Asp-Glu-Nle-D-Phe-Thr-Ile-Leu-Asp-Phe-Leu-Ala-Ala-Arg-Asp-Phe-Ile-Asn-Trp-Leu-Ile-Gln-Thr-Lys-Ile-Thr-Asp-NH—CH$_2$—((CH$_2$)$_2$O)$_3$—(CH$_2$)$_3$—NHCO—CH$_2$—O—CH$_2$—CONH$_2$,
    His-Gly-Asp-Gly-Ser-Phe-Ser-Asp-Glu-Nle-D-Phe-Thr-Ile-Leu-Asp-Phe-Leu-Ala-Ala-Arg-Asp-Phe-Ile-Asn-Trp-Leu-Ile-Gln-Thr-Lys-Ile-Thr-Asp-NH—CH$_2$—((CH$_2$)$_2$O)$_3$—(CH$_2$)$_3$—NHCO—CH$_2$—O—CH$_2$—CONH—((CH$_2$)$_2$O)$_6$—(CH$_2$)$_2$—CONH$_2$
    His-Gly-Asp-Gly-Ser-Phe-Ser-Asp-Glu-Nle-D-Thi-Thr-Ile-Leu-Asp-Leu-Leu-Ala-Thr-Arg-Asp-Phe-Ile-Asn-Trp-Leu-Ile-Gln-Thr-Lys-Ile-Thr-Asp-NH$_2$,
    His-Gly-Asp-Gly-Ser-Phe-Ser-Asp-Glu-Nle-D-Phe-Thr-Ile-Leu-Asp-Phe-Leu-Ala-Ala-Arg-Asp-Phe-Ile-Asn-Trp-Leu-Ile-Gln-Thr-Lys-Ile-Thr-Asp-NH$_2$,
    His-Gly-Asp-Gly-Ser-Phe-Ser-Asp-Glu-Nle-D-Phe-Thr-Ile-Leu-Asp-Phe-Leu-Ala-Ala-Arg-Asp-Phe-Ile-Asn-Trp-Leu-Ile-Gln-Thr-Lys-Ile-Thr-Asp-OH, and
    His-Gly-Asp-Gly-Ser-Phe-Ser-Asp-Glu-Nle-D-Thi-Thr-Ile-Leu-Asp-Phe-Leu-Ala-Ala-Arg-Asp-Phe-Ile-Asn-Trp-Leu-Ile-Gln-Thr-Lys-Ile-Thr-Asp-NH$_2$.

14. The compound of claim 11 wherein $X_2$ is Ile, $X_3$ is Thr and $X_4$ is Asp.

15. The compound of claim 11 wherein $X_2$, $X_3$, and $X_4$ are all present.

16. The compound of claim 11 wherein Z is OH or $NH_2$.

17. The compound of claim 11 wherein Z is $NR^9$, $R^{10}$ and $R^9$ is hydrogen and $R^{10}$ is aralkyl or alkyl.

18. A pharmaceutical composition comprising the compound claim 1.

19. A pharmaceutical composition comprising the compound of claim 1 as active ingredient in association with a pharmaceutically acceptable adjuvant, diluent or carrier.

20. A method of treating an animal patient in need of treatment for one of the group consisting of gastrointestinal injury, diarrheal diseases, intestinal insufficiency, acid-induced intestinal injury, arginine deficiency, idiopathic hypospermia, obesity, celiac disease, catabolic illness, chemotherapy-induced enteritis, febrile neutropenia, diabetes, obesity, fat malabsorption, steatorrhea, autoimmune diseases, food allergies, gastric ulcers, hypoglycemia, gastrointestinal barrier disorders, sepsis, bacterial peritonitis, burn-induced intestinal damage, decreased gastrointestinal motility, inflammatory bowel disease, intestinal failure, chemotherapy-associated bacteremia, bowel trauma, bowel ischemia, mesenteric ischemia, irritable bowel syndrome, short bowel syndrome, malnutrition, necrotizing enterocolitis, necrotizing pancreatitis, neonatal feeding intolerance, NSAID-induced gastrointestinal damage, nutritional insufficiency, total parenteral nutrition damage to gastrointestinal tract, neonatal nutritional insufficiency, radiation-induced enteritis, radiation-induced injury to the intestines, mucositis, pouchitis, ischemia, and stroke, the method comprising administering to the patient, a therapeutically effective amount of the compound according to claim 1.

21. The method of claim 20 wherein inflammatory bowel disease comprises Crohn's Disease or ulcerative colitis.

22. A method of, in an animal patient in need thereof, regulating appetite; enhancing, stimulating or accelerating weight loss; enhancing, stimulating or accelerating gastric relaxation; controlling glucose levels; enhancing, stimulating or accelerating hunger satiety; enhancing intestinal immune function; enhancing, stimulating or accelerating intestinal wound healing; enhancing, stimulating or accelerating juvenile weight loss; enhancing, stimulating or accelerating weight loss; enhancing, stimulating or accelerating neonatal bowel development; enhancing, stimulating or accelerating fetal or neonatal development; treating intestinal cancers; enhancing or stimulating mucosal integrity; minimizing, mitigating, or preventing bacterial translocation in the intestines; enhancing, stimulating or accelerating recovery of the intestines after surgery; preventing relapses of inflammatory bowel disease; or achieving or maintaining energy homeostasis, the method comprising administering to the patient, a therapeutically effective amount of a compound according to claim 1.

23. The method of claim 22 wherein inflammatory bowel disease comprises Crohn's Disease or ulcerative colitis.

24. A method of treating an animal patient in need of treatment for one of the group consisting of depression, autism, osteoporosis, and traumatic brain injury, the method comprising administering to the patient, a therapeutically effective amount of a compound according to claim 1.

25. A method of, in an animal patient in need thereof, enhancing, stimulating or accelerating astroglial regeneration or enhancing, stimulating or accelerating repair or growth of the central nervous system; the method comprising administering to the patient, a therapeutically effective amount of a compound according to claim 1.

26. The method of claim 20 wherein the animal patient is a human patient.

27. The method of claim 22 wherein the animal patient is a human patient.

28. The method of claim 24 wherein the animal patient is a human patient.

29. The method of claim 25 wherein the animal patient is a human patient.

30. The compound of claim 12 which is:
His-Gly-Asp-Gly-Ser-Phe-Ser-Asp-Glu-Nle-D-Phe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-NH$_2$.

31. The method of claim 26 wherein the compound is:
His-Gly-Asp-Gly-Ser-Phe-Ser-Asp-Glu-Nle-D-Phe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-NH$_2$.

32. The method of claim 27 wherein the compound is:
His-Gly-Asp-Gly-Ser-Phe-Ser-Asp-Glu-Nle-D-Phe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-NH$_2$.

33. The method of claim 28 wherein the compound is:
His-Gly-Asp-Gly-Ser-Phe-Ser-Asp-Glu-Nle-D-Phe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-NH$_2$.

34. The method of claim 29 wherein the compound is:
His-Gly-Asp-Gly-Ser-Phe-Ser-Asp-Glu-Nle-D-Phe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-NH$_2$.

35. The method of claim 21 wherein the animal patient is a human patient and wherein the compound is:
His-Gly-Asp-Gly-Ser-Phe-Ser-Asp-Glu-Nle-D-Phe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-NH$_2$.

36. The method of claim 23 wherein the animal patient is a human patient and wherein the compound is:
His-Gly-Asp-Gly-Ser-Phe-Ser-Asp-Glu-Nle-D-Phe-Thr-Ile-Leu-Asp-Leu-Leu-Ala-Ala-Arg-Asp-Phe-Ile-Asn-Trp-Leu-Ile-Gln-Thr-Lys-Ile-Thr-Asp-NH$_2$.

\* \* \* \* \*

UNITED STATES PATENT AND TRADEMARK OFFICE
CERTIFICATE OF CORRECTION

| | | |
|---|---|---|
| PATENT NO. | : 8,580,918 B2 | Page 1 of 1 |
| APPLICATION NO. | : 13/503010 | |
| DATED | : November 12, 2013 | |
| INVENTOR(S) | : Sudarkodi Alagarsamy et al. | |

It is certified that error appears in the above-identified patent and that said Letters Patent is hereby corrected as shown below:

In the Claims

Column 77, Claim 1, after "A compound of formula I:", replace three instances of labeling "Ile" in the figure with --Ile--; and Column 79, Claim 11, line 23, after "0, R5" insert --is--; and Column 79, Claim 11, line 23, after "1, R7" insert --is--; and Column 79, Claim 12, line 36, replace "N H2" with --NH2--; and Column 80, Claim 13, line 2, after "CONH2" insert --,--; and Column 80, Claim 18, line 24, after "pound" insert --of--.

Signed and Sealed this
Fifth Day of May, 2015

Michelle K. Lee
*Director of the United States Patent and Trademark Office*

SEQUENCE LISTING

```
<160> NUMBER OF SEQ ID NOS: 74

<210> SEQ ID NO 1
<211> LENGTH: 33
<212> TYPE: PRT
<213> ORGANISM: Homo sapiens

<400> SEQUENCE: 1

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

```
Ser Phe Ser Asp Glu
1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Ile Leu Asp
1

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Gln or Arg
<220> FEATURE:
<221> NAME/KEY: MOD_RES
<222> LOCATION: (12)..(14)
<223> OTHER INFORMATION: Val, Leu, Ile, Ser, Thr, Asp, Glu or absent
<220> FEATURE:
<223> OTHER INFORMATION: see specification as filed for detailed
      description of substitutions and preferred embodiments

<400> SEQUENCE: 4

Arg Asp Phe Ile Asn Trp Leu Ile Xaa Thr Lys Xaa Xaa Xaa
1               5                   10

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (10)..(10)
<223> OTHER INFORMATION: Nle
<220> FEATURE:
<223> OTHER INFORMATION: C-term amidated

<400> SEQUENCE: 5

His Gly Asp Xaa Ser Phe Ser Asp Glu Xaa Asn Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (1)..(1)
<223> OTHER INFORMATION: 2-PhEtHis
<220> FEATURE:
<221> NAME/KEY: MOD_RES
<222> LOCATION: (10)..(10)
<223> OTHER INFORMATION: Nle
<220> FEATURE:
<223> OTHER INFORMATION: C-term amidated

<400> SEQUENCE: 6

Xaa Ala Asp Gly Ser Phe Ser Asp Glu Xaa Asn Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 3-MeBuHis
<220> FEATURE:
<221> NAME/KEY: MOD_RES
<222> LOCATION: (10)..(10)
<223> OTHER INFORMATION: Nle
<220> FEATURE:
<223> OTHER INFORMATION: C-term amidated

<400> SEQUENCE: 7

Xaa Ala Asp Gly Ser Phe Ser Asp Glu Xaa Asn Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: OctHis
<220> FEATURE:
<221> NAME/KEY: MOD_RES
<222> LOCATION: (10)..(10)
<223> OTHER INFORMATION: Nle
<220> FEATURE:
<223> OTHER INFORMATION: C-term amidated

<400> SEQUENCE: 8

Xaa Ala Asp Gly Ser Phe Ser Asp Glu Xaa Asn Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (10)..(10)
<223> OTHER INFORMATION: Nle
<220> FEATURE:
<223> OTHER INFORMATION: C-term NH-i-Am

<400> SEQUENCE: 9

His Gly Asp Gly Ser Phe Ser Asp Glu Xaa Asn Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<223> OTHER INFORMATION: C-term NH-Et

<400> SEQUENCE: 10

His Gly Asp Gly Ser Phe Ser Asp Glu Xaa Asn Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<223> OTHER INFORMATION: C-term NH-Bzl

<400> SEQUENCE: 11

His Gly Asp Gly Ser Phe Ser Asp Glu Xaa Asn Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (16)..(16)
<223> OTHER INFORMATION: D-Phe
<220> FEATURE:
<223> OTHER INFORMATION: C-term amidated

<400> SEQUENCE: 12
```

His Gly Asp Gly Ser Phe Ser Asp Glu Xaa Asn Thr Ile Leu Asp Xaa
1               5                   10                  15

Leu Ala Ala Arg Asp Phe Ile Asn Trp Leu Ile Gln Thr Lys
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<223> OTHER INFORMATION: C-term amidated

<400> SEQUENCE: 13

His Gly Asp Gly Ser Phe Ser Asp Glu Xaa Asn Thr Ile Leu Asp Phe
1               5                   10                  15

Leu Ala Ala Arg Asp Phe Ile Asn Trp Leu Ile Gln Thr Lys
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<223> OTHER INFORMATION: C-term NH-i-Am

<400> SEQUENCE: 14

His Gly Asp Gly Ser Phe Ser Asp Glu Xaa Asn Thr Ile Leu Asp Asn
1               5                   10                  15

Leu Ala Ala Arg Asp Phe Ile Asn Trp Leu Ile Arg Thr Lys
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<223> OTHER INFORMATION: C-term amidated

<400> SEQUENCE: 15

His Gly Asp Gly Ser Phe Ser Asp Glu Xaa Asn Thr Ile Leu Asp Leu
1               5                   10                  15

Leu Ala Ala Arg Asp Phe Ile Asn Trp Leu Ile Gln Thr Lys
            20                  25                  30

<210> SEQ ID NO 16
<211> LENGTH: 30
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Asn
<220> FEATURE:
<223> OTHER INFORMATION: C-term NH-i-Am

<400> SEQUENCE: 16

His Gly Asp Gly Ser Phe Ser Asp Glu Xaa Xaa Thr Ile Leu Asp Asn
1               5                  10                  15

Leu Ala Ala Arg Asp Phe Ile Asn Trp Leu Ile Gln Thr Lys
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term amidated

<400> SEQUENCE: 17

His Gly Asp Gly Ser Phe Ser Asp Glu Xaa Xaa Thr Ile Leu Asp Asn
1               5                  10                  15

Leu Ala Ala Arg Asp Phe Ile Asn Trp Leu Ile Gln Thr Lys
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<223> OTHER INFORMATION: C-term amidated

<400> SEQUENCE: 18

His Gly Asp Gly Ser Phe Ser Asp Glu Xaa Phe Thr Ile Leu Asp Asn
1               5                  10                  15

Leu Ala Ala Arg Asp Phe Ile Asn Trp Leu Ile Gln Thr Lys
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
```

```
      polypeptide
<220> FEATURE:
<221> NAME/KEY: MOD_RES
<222> LOCATION: (10)..(10)
<223> OTHER INFORMATION: Nle
<220> FEATURE:
<223> OTHER INFORMATION: C-term amidated

<400> SEQUENCE: 19

His Gly Asp Gly Ser Phe Ser Asp Glu Xaa Leu Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Leu
<220> FEATURE:
<223> OTHER INFORMATION: C-term amidated

<400> SEQUENCE: 20

His Gly Asp Gly Ser Phe Ser Asp Glu Xaa Xaa Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (16)..(16)
<223> OTHER INFORMATION: 1-Nal
<220> FEATURE:
<223> OTHER INFORMATION: C-term amidated

<400> SEQUENCE: 21

His Gly Asp Gly Ser Phe Ser Asp Glu Xaa Asn Thr Ile Leu Asp Xaa
1               5                   10                  15

Leu Ala Ala Arg Asp Phe Ile Asn Trp Leu Ile Gln Thr Lys
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (10)..(10)
<223> OTHER INFORMATION: Nle
<220> FEATURE:
<223> OTHER INFORMATION: C-term amidated

<400> SEQUENCE: 22

His Gly Asp Gly Ser Phe Ser Asp Glu Xaa Asn Thr Ile Leu Asp Tyr
1               5                   10                  15

Leu Ala Ala Arg Asp Phe Ile Asn Trp Leu Ile Gln Thr Lys
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<223> OTHER INFORMATION: C-term amidated

<400> SEQUENCE: 23

His Gly Asp Gly Ser Phe Ser Asp Glu Xaa Asn Thr Ile Leu Asp His
1               5                   10                  15

Leu Ala Ala Arg Asp Phe Ile Asn Trp Leu Ile Gln Thr Lys
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (16)..(16)
<223> OTHER INFORMATION: 2-Nal
<220> FEATURE:
<223> OTHER INFORMATION: C-term amidated

<400> SEQUENCE: 24

His Gly Asp Gly Ser Phe Ser Asp Glu Xaa Asn Thr Ile Leu Asp Xaa
1               5                   10                  15

Leu Ala Ala Arg Asp Phe Ile Asn Trp Leu Ile Gln Thr Lys
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (16)..(16)
<223> OTHER INFORMATION: Thi
<220> FEATURE:
```

<223> OTHER INFORMATION: C-term amidated

<400> SEQUENCE: 25

His Gly Asp Gly Ser Phe Ser Asp Glu Xaa Asn Thr Ile Leu Asp Xaa
1               5                   10                  15

Leu Ala Ala Arg Asp Phe Ile Asn Trp Leu Ile Gln Thr Lys
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<223> OTHER INFORMATION: C-term amidated

<400> SEQUENCE: 26

His Gly Asp Gly Ser Phe Ser Asp Glu Xaa Asn Thr Ile Leu Asp Trp
1               5                   10                  15

Leu Ala Ala Arg Asp Phe Ile Asn Trp Leu Ile Gln Thr Lys
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (16)..(16)
<223> OTHER INFORMATION: Cha
<220> FEATURE:
<223> OTHER INFORMATION: C-term amidated

<400> SEQUENCE: 27

His Gly Asp Gly Ser Phe Ser Asp Glu Xaa Asn Thr Ile Leu Asp Xaa
1               5                   10                  15

Leu Ala Ala Arg Asp Phe Ile Asn Trp Leu Ile Gln Thr Lys
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (16)..(16)
<223> OTHER INFORMATION: Aph
<220> FEATURE:
<223> OTHER INFORMATION: C-term amidated

<400> SEQUENCE: 28

His Gly Asp Gly Ser Phe Ser Asp Glu Xaa Asn Thr Ile Leu Asp Xaa
1               5                   10                  15

Leu Ala Ala Arg Asp Phe Ile Asn Trp Leu Ile Gln Thr Lys
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (16)..(16)
<223> OTHER INFORMATION: Cpa
<220> FEATURE:
<223> OTHER INFORMATION: C-term amidated

<400> SEQUENCE: 29

His Gly Asp Gly Ser Phe Ser Asp Glu Xaa Asn Thr Ile Leu Asp Xaa
1               5                   10                  15

Leu Ala Ala Arg Asp Phe Ile Asn Trp Leu Ile Gln Thr Lys
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (16)..(16)
<223> OTHER INFORMATION: Dip
<220> FEATURE:
<223> OTHER INFORMATION: C-term amidated

<400> SEQUENCE: 30

His Gly Asp Gly Ser Phe Ser Asp Glu Xaa Asn Thr Ile Leu Asp Xaa
1               5                   10                  15

Leu Ala Ala Arg Asp Phe Ile Asn Trp Leu Ile Gln Thr Lys
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (16)..(16)
<223> OTHER INFORMATION: Bip
<220> FEATURE:
<223> OTHER INFORMATION: C-term amidated -continued

```
<400> SEQUENCE: 31

His Gly Asp Gly Ser Phe Ser Asp Glu Xaa Asn Thr Ile Leu Asp Xaa
1               5                   10                  15

Leu Ala Ala Arg Asp Phe Ile Asn Trp Leu Ile Gln Thr Lys
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (16)..(16)
<223> OTHER INFORMATION: hPhe
<220> FEATURE:
<223> OTHER INFORMATION: C-term amidated

<400> SEQUENCE: 32

His Gly Asp Gly Ser Phe Ser Asp Glu Xaa Asn Thr Ile Leu Asp Xaa
1               5                   10                  15

Leu Ala Ala Arg Asp Phe Ile Asn Trp Leu Ile Gln Thr Lys
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Cpa
<220> FEATURE:
<223> OTHER INFORMATION: C-term amidated

<400> SEQUENCE: 33

His Gly Asp Gly Ser Phe Ser Asp Glu Xaa Xaa Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Trp
<220> FEATURE:
<223> OTHER INFORMATION: C-term amidated
```

<400> SEQUENCE: 34

His Gly Asp Gly Ser Phe Ser Asp Glu Xaa Xaa Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<223> OTHER INFORMATION: C-term amidated

<400> SEQUENCE: 35

His Gly Asp Gly Ser Phe Ser Asp Glu Xaa Ile Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Thi
<220> FEATURE:
<223> OTHER INFORMATION: C-term amidated

<400> SEQUENCE: 36

His Gly Asp Gly Ser Phe Ser Asp Glu Xaa Xaa Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: Cpa
<220> FEATURE:
<223> OTHER INFORMATION: C-term amidated

<400> SEQUENCE: 37

His Gly Asp Gly Ser Phe Ser Asp Glu Xaa Xaa Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<223> OTHER INFORMATION: C-term amidated

<400> SEQUENCE: 38

His Gly Asp Gly Ser Phe Ser Asp Glu Xaa His Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-His
<220> FEATURE:
<223> OTHER INFORMATION: C-term amidated

<400> SEQUENCE: 39

His Gly Asp Gly Ser Phe Ser Asp Glu Xaa Xaa Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: Cha
<220> FEATURE:
<223> OTHER INFORMATION: C-term amidated

<400> SEQUENCE: 40

His Gly Asp Gly Ser Phe Ser Asp Glu Xaa Xaa Thr Ile Leu Asp Asn
1               5                   10                  15

```
Leu Ala Ala Arg Asp Phe Ile Asn Trp Leu Ile Gln Thr Lys
         20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: Hol
<220> FEATURE:
<223> OTHER INFORMATION: C-term amidated

<400> SEQUENCE: 41

His Gly Asp Gly Ser Phe Ser Asp Glu Xaa Xaa Thr Ile Leu Asp Asn
1               5                   10                  15

Leu Ala Ala Arg Asp Phe Ile Asn Trp Leu Ile Gln Thr Lys
         20                  25                  30

<210> SEQ ID NO 42
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: Bip
<220> FEATURE:
<223> OTHER INFORMATION: C-term amidated

<400> SEQUENCE: 42

His Gly Asp Gly Ser Phe Ser Asp Glu Xaa Xaa Thr Ile Leu Asp Asn
1               5                   10                  15

Leu Ala Ala Arg Asp Phe Ile Asn Trp Leu Ile Gln Thr Lys
         20                  25                  30

<210> SEQ ID NO 43
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Tyr
<220> FEATURE:
<223> OTHER INFORMATION: C-term amidated

<400> SEQUENCE: 43

His Gly Asp Gly Ser Phe Ser Asp Glu Xaa Xaa Thr Ile Leu Asp Asn
1               5                   10                  15
```

```
Leu Ala Ala Arg Asp Phe Ile Asn Trp Leu Ile Gln Thr Lys
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-2-Cpa
<220> FEATURE:
<223> OTHER INFORMATION: C-term amidated

<400> SEQUENCE: 44

His Gly Asp Gly Ser Phe Ser Asp Glu Xaa Xaa Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Fpa
<220> FEATURE:
<223> OTHER INFORMATION: C-term amidated

<400> SEQUENCE: 45

His Gly Asp Gly Ser Phe Ser Asp Glu Xaa Xaa Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-3-Thi
<220> FEATURE:
<223> OTHER INFORMATION: C-term amidated

<400> SEQUENCE: 46

His Gly Asp Gly Ser Phe Ser Asp Glu Xaa Xaa Thr Ile Leu Asp Asn
```

```
1               5                   10                  15
Leu Ala Ala Arg Asp Phe Ile Asn Trp Leu Ile Gln Thr Lys
            20                  25                  30

<210> SEQ ID NO 47
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-FurAla
<220> FEATURE:
<223> OTHER INFORMATION: C-term amidated

<400> SEQUENCE: 47

His Gly Asp Gly Ser Phe Ser Asp Glu Xaa Xaa Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 48
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-3-Cpa
<220> FEATURE:
<223> OTHER INFORMATION: C-term amidated

<400> SEQUENCE: 48

His Gly Asp Gly Ser Phe Ser Asp Glu Xaa Xaa Thr Ile Leu Asp Asn
1               5                   10                  15

Leu Ala Ala Arg Asp Phe Ile Asn Trp Leu Ile Gln Thr Lys
            20                  25                  30

<210> SEQ ID NO 49
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Thi
<220> FEATURE:
<223> OTHER INFORMATION: C-term amidated

<400> SEQUENCE: 49
```

His Gly Asp Gly Ser Phe Ser Asp Glu Xaa Xaa Thr Ile Leu Asp Leu
1               5                   10                  15

Leu Ala Ala Arg Asp Phe Ile Asn Trp Leu Ile Gln Thr Lys
            20                  25                  30

<210> SEQ ID NO 50
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Thi
<220> FEATURE:
<223> OTHER INFORMATION: C-term amidated

<400> SEQUENCE: 50

His Gly Asp Gly Ser Phe Ser Asp Glu Xaa Xaa Thr Ile Leu Asp Phe
1               5                   10                  15

Leu Ala Ala Arg Asp Phe Ile Asn Trp Leu Ile Gln Thr Lys
            20                  25                  30

<210> SEQ ID NO 51
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term amidated

<400> SEQUENCE: 51

His Gly Asp Gly Ser Phe Ser Asp Glu Xaa Xaa Thr Ile Leu Asp Phe
1               5                   10                  15

Leu Ala Ala Arg Asp Phe Ile Asn Trp Leu Ile Gln Thr Lys
            20                  25                  30

<210> SEQ ID NO 52
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term amidated

<400> SEQUENCE: 52

```
His Gly Asp Gly Ser Phe Ser Asp Glu Xaa Xaa Thr Ile Leu Asp Leu
1               5                   10                  15

Leu Ala Ala Arg Asp Phe Ile Asn Trp Leu Ile Gln Thr Lys
            20                  25                  30

<210> SEQ ID NO 53
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term amidated

<400> SEQUENCE: 53

His Gly Asp Gly Ser Phe Ser Asp Glu Xaa Xaa Thr Ile Leu Asp Tyr
1               5                   10                  15

Leu Ala Ala Arg Asp Phe Ile Asn Trp Leu Ile Gln Thr Lys
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Thi
<220> FEATURE:
<223> OTHER INFORMATION: C-term amidated

<400> SEQUENCE: 54

His Gly Asp Gly Ser Phe Ser Asp Glu Xaa Xaa Thr Ile Leu Asp Tyr
1               5                   10                  15

Leu Ala Ala Arg Asp Phe Ile Asn Trp Leu Ile Gln Thr Lys
            20                  25                  30

<210> SEQ ID NO 55
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term amidated
```

```
<400> SEQUENCE: 55

His Gly Asp Gly Ser Phe Ser Asp Glu Xaa Xaa Thr Ile Leu Asp Leu
1               5                   10                  15

Leu Ala Ala Arg Asp Phe Ile Asn Trp Leu Ile Gln Thr Lys Ile Thr
            20                  25                  30

Asp

<210> SEQ ID NO 56
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term amidated

<400> SEQUENCE: 56

His Gly Asp Gly Ser Phe Ser Asp Glu Xaa Xaa Thr Ile Leu Asp Leu
1               5                   10                  15

Leu Ala Thr Arg Asp Phe Ile Asn Trp Leu Ile Gln Thr Lys
            20                  25                  30

<210> SEQ ID NO 57
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term NHEt

<400> SEQUENCE: 57

His Gly Asp Gly Ser Phe Ser Asp Glu Xaa Xaa Thr Ile Leu Asp Leu
1               5                   10                  15

Leu Ala Ala Arg Asp Phe Ile Asn Trp Leu Ile Gln Thr Lys Ile Thr
            20                  25                  30

Asp

<210> SEQ ID NO 58
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
```

```
<222> LOCATION: (11)..(11)
<223> OTHER INFORMATION: D-Phe
<220> FEATURE:
<223> OTHER INFORMATION: C-term NH-4-Pic

<400> SEQUENCE: 58

His Gly Asp Gly Ser Phe Ser Asp Glu Xaa Xaa Thr Ile Leu Asp Leu
1               5                   10                  15

Leu Ala Ala Arg Asp Phe Ile Asn Trp Leu Ile Gln Thr Lys Ile Thr
            20                  25                  30

Asp

<210> SEQ ID NO 59
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term NH-((CH2)2O)4-(CH2)2-C(O)-NH2

<400> SEQUENCE: 59

His Gly Asp Gly Ser Phe Ser Asp Glu Xaa Xaa Thr Ile Leu Asp Leu
1               5                   10                  15

Leu Ala Ala Arg Asp Phe Ile Asn Trp Leu Ile Gln Thr Lys Ile Thr
            20                  25                  30

Asp

<210> SEQ ID NO 60
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term NH-CH2-((CH2)2O)3-(CH2)3-NHC(O)-CH2-O-
      CH2-C(O)-NH2

<400> SEQUENCE: 60

His Gly Asp Gly Ser Phe Ser Asp Glu Xaa Xaa Thr Ile Leu Asp Leu
1               5                   10                  15

Leu Ala Ala Arg Asp Phe Ile Asn Trp Leu Ile Gln Thr Lys Ile Thr
            20                  25                  30

Asp

<210> SEQ ID NO 61
<211> LENGTH: 33
<212> TYPE: PRT
<213> ORGANISM: Artificial Sequence
<220> FEATURE:
```

-continued

<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term NH-isobutyl

<400> SEQUENCE: 61

His Gly Asp Gly Ser Phe Ser Asp Glu Xaa Xaa Thr Ile Leu Asp Leu
1               5                   10                  15

Leu Ala Ala Arg Asp Phe Ile Asn Trp Leu Ile Gln Thr Lys Ile Thr
            20                  25                  30

Asp

<210> SEQ ID NO 62
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term NH-Benzyl

<400> SEQUENCE: 62

His Gly Asp Gly Ser Phe Ser Asp Glu Xaa Xaa Thr Ile Leu Asp Leu
1               5                   10                  15

Leu Ala Ala Arg Asp Phe Ile Asn Trp Leu Ile Gln Thr Lys Ile Thr
            20                  25                  30

Asp

<210> SEQ ID NO 63
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term OH

<400> SEQUENCE: 63

His Gly Asp Gly Ser Phe Ser Asp Glu Xaa Xaa Thr Ile Leu Asp Leu
1               5                   10                  15

Leu Ala Ala Arg Asp Phe Ile Asn Trp Leu Ile Gln Thr Lys Ile Thr
            20                  25                  30

Asp

```
<210> SEQ ID NO 64
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term NH-CH2-((CH2)2O)3-(CH2)3-NH-C(O)-CH2-O-
      CH2-C(O)-NH2

<400> SEQUENCE: 64

His Gly Asp Gly Ser Phe Ser Asp Glu Xaa Xaa Thr Ile Leu Asp Phe
1               5                   10                  15

Leu Ala Ala Arg Asp Phe Ile Asn Trp Leu Ile Gln Thr Lys Ile Thr
            20                  25                  30

Asp

<210> SEQ ID NO 65
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term NH-CH2-((CH2)2O)3-(CH2)3-NH-C(O)-CH2-O-
      CH2-C(O)-NH-((CH2)2O)6-(CH2)2-C(O)-NH2

<400> SEQUENCE: 65

His Gly Asp Gly Ser Phe Ser Asp Glu Xaa Xaa Thr Ile Leu Asp Phe
1               5                   10                  15

Leu Ala Ala Arg Asp Phe Ile Asn Trp Leu Ile Gln Thr Lys Ile Thr
            20                  25                  30

Asp

<210> SEQ ID NO 66
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Thi
<220> FEATURE:
<223> OTHER INFORMATION: C-term amidated
```

-continued

```
<400> SEQUENCE: 66

His Gly Asp Gly Ser Phe Ser Asp Glu Xaa Xaa Thr Ile Leu Asp Leu
1               5                   10                  15

Leu Ala Thr Arg Asp Phe Ile Asn Trp Leu Ile Gln Thr Lys Ile Thr
            20                  25                  30

Asp

<210> SEQ ID NO 67
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term amidated

<400> SEQUENCE: 67

His Gly Asp Gly Ser Phe Ser Asp Glu Xaa Xaa Thr Ile Leu Asp Phe
1               5                   10                  15

Leu Ala Ala Arg Asp Phe Ile Asn Trp Leu Ile Gln Thr Lys Ile Thr
            20                  25                  30

Asp

<210> SEQ ID NO 68
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term OH

<400> SEQUENCE: 68

His Gly Asp Gly Ser Phe Ser Asp Glu Xaa Xaa Thr Ile Leu Asp Phe
1               5                   10                  15

Leu Ala Ala Arg Asp Phe Ile Asn Trp Leu Ile Gln Thr Lys Ile Thr
            20                  25                  30

Asp

<210> SEQ ID NO 69
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
```

```
<220> FEATURE:
<221> NAME/KEY: MOD_RES
<222> LOCATION: (11)..(11)
<223> OTHER INFORMATION: D-3-Cpa
<220> FEATURE:
<221> NAME/KEY: MOD_RES
<222> LOCATION: (16)..(16)
<223> OTHER INFORMATION: 2-Nal
<220> FEATURE:
<223> OTHER INFORMATION: C-term amidated

<400> SEQUENCE: 69

His Gly Asp Gly Ser Phe Ser Asp Glu Xaa Xaa Thr Ile Leu Asp Xaa
1               5                   10                  15

Leu Ala Ala Arg Asp Phe Ile Asn Trp Leu Ile Gln Thr Lys Ile Thr
            20                  25                  30

Asp

<210> SEQ ID NO 70
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-3-Cpa
<220> FEATURE:
<223> OTHER INFORMATION: C-term amidated

<400> SEQUENCE: 70

His Gly Asp Gly Ser Phe Ser Asp Glu Xaa Xaa Thr Ile Leu Asp Phe
1               5                   10                  15

Leu Ala Ala Arg Asp Phe Ile Asn Trp Leu Ile Gln Thr Lys Ile Thr
            20                  25                  30

Asp

<210> SEQ ID NO 71
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-3-Cpa
<220> FEATURE:
<223> OTHER INFORMATION: C-term amidated

<400> SEQUENCE: 71

His Gly Asp Gly Ser Phe Ser Asp Glu Xaa Xaa Thr Ile Leu Asp Leu
1               5                   10                  15

Leu Ala Ala Arg Asp Phe Ile Asn Trp Leu Ile Gln Thr Lys Ile Thr
            20                  25                  30

Asp
```

```
<210> SEQ ID NO 72
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Thi
<220> FEATURE:
<223> OTHER INFORMATION: C-term amidated

<400> SEQUENCE: 72

His Gly Asp Gly Ser Phe Ser Asp Glu Xaa Xaa Thr Ile Leu Asp Phe
1               5                   10                  15

Leu Ala Ala Arg Asp Phe Ile Asn Trp Leu Ile Gln Thr Lys Ile Thr
            20                  25                  30

Asp

<210> SEQ ID NO 73
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term amidated

<400> SEQUENCE: 73

His Gly Asp Xaa Ser Phe Ser Asp Glu Xaa Xaa Thr Ile Leu Asp Leu
1               5                   10                  15

Leu Ala Ala Arg Asp Phe Ile Asn Trp Leu Ile Gln Thr Lys Ile Thr
            20                  25                  30

Asp

<210> SEQ ID NO 74
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: EtHis
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (10)..(10)
```

```
<223> OTHER INFORMATION: Nle
<220> FEATURE:
<221> NAME/KEY: MOD_RES
<222> LOCATION: (11)..(11)
<223> OTHER INFORMATION: D-Phe
<220> FEATURE:
<223> OTHER INFORMATION: C-term amidated

<400> SEQUENCE: 74

Xaa Ala Asp Xaa Ser Phe Ser Asp Glu Xaa Xaa Thr Ile Leu Asp Leu
 1               5                  10                  15

Leu Ala Ala Arg Asp Phe Ile Asn Trp Leu Ile Gln Thr Lys Ile Thr
                20                  25                  30

Asp
```